United States Patent
Fultz et al.

(10) Patent No.: US 9,737,535 B2
(45) Date of Patent: Aug. 22, 2017

(54) METHODS FOR TREATING CANCER USING TOR KINASE INHIBITOR COMBINATION THERAPY COMPRISING ADMINISTERING SUBSTITUTED PYRAZINO[2,3-B]PYRAZINES

(71) Applicant: Signal Pharmaceuticals, LLC, San Diego, CA (US)

(72) Inventors: Kimberly Elizabeth Fultz, San Diego, CA (US); Tam Minh Tran, San Diego, CA (US); Shuichan Xu, San Diego, CA (US); Weiming Xu, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 124 days.

(21) Appl. No.: 14/686,872

(22) Filed: Apr. 15, 2015

(65) Prior Publication Data

US 2015/0297590 A1 Oct. 22, 2015

Related U.S. Application Data

(60) Provisional application No. 61/980,124, filed on Apr. 16, 2014.

(51) Int. Cl.

| | | |
|---|---|---|
| *C07D 487/04* | (2006.01) | |
| *C07D 401/14* | (2006.01) | |
| *C07D 249/08* | (2006.01) | |
| *A61K 31/4985* | (2006.01) | |
| *A61K 31/517* | (2006.01) | |
| *A61K 31/44* | (2006.01) | |
| *A61K 31/4184* | (2006.01) | |
| *A61K 31/501* | (2006.01) | |
| *A61K 31/69* | (2006.01) | |
| *A61K 38/14* | (2006.01) | |
| *A61K 31/7048* | (2006.01) | |
| *A61K 31/704* | (2006.01) | |
| *A61K 31/282* | (2006.01) | |
| *A61K 31/337* | (2006.01) | |
| *A61K 31/519* | (2006.01) | |

(52) U.S. Cl.
CPC ........ *A61K 31/4985* (2013.01); *A61K 31/282* (2013.01); *A61K 31/337* (2013.01); *A61K 31/4184* (2013.01); *A61K 31/44* (2013.01); *A61K 31/501* (2013.01); *A61K 31/517* (2013.01); *A61K 31/519* (2013.01); *A61K 31/69* (2013.01); *A61K 31/704* (2013.01); *A61K 31/7048* (2013.01); *A61K 38/14* (2013.01)

(58) Field of Classification Search
CPC ... C07D 249/08; C07D 401/14; C07D 487/04
USPC ............... 544/350; 546/272.4; 548/266.4
See application file for complete search history.

(56) References Cited

U.S. PATENT DOCUMENTS

| | | |
|---|---|---|
| 3,507,866 A | 4/1970 | Jones et al. |
| 3,567,725 A | 3/1971 | Grabowki et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,855,723 B2 | 2/2005 | McMahon et al. |
| 7,651,687 B2 | 1/2010 | Buck et al. |
| 7,968,556 B2 | 6/2011 | Mortensen et al. |
| 7,981,893 B2 | 7/2011 | Mortensen et al. |
| 8,110,578 B2 | 2/2012 | Perrin-Ninkovic et al. |
| 8,372,976 B2 | 2/2013 | Mortensen et al. |
| 8,383,634 B2 | 2/2013 | Mortensen et al. |

(Continued)

FOREIGN PATENT DOCUMENTS

| | | |
|---|---|---|
| CA | 2 458 699 A1 | 3/2003 |
| DE | 262 026 | 11/1988 |

(Continued)

OTHER PUBLICATIONS

Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*
Figlin et al., 2013, Targeting PI3K and mTORC2 in metastatic renal cell carcinoma: New strategies for overcoming resistance to VEGFR and mTORC1 inhibitors, *Int. J. Cancer*, 2013, vol. 133, pp. 788-796.

(Continued)

*Primary Examiner* — Douglas M Willis
(74) *Attorney, Agent, or Firm* — Jones Day

(57) ABSTRACT

Provided herein are methods for treating or preventing a cancer, comprising administering an effective amount of a TOR kinase inhibitor and an effective amount a second active agent to a patient having a cancer, wherein the TOR kinase inhibitor is a compound of formula (I):

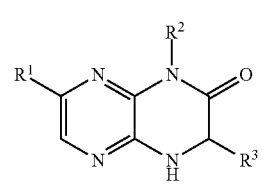

and pharmaceutically acceptable salts, clathrates, solvates, stereoisomers, tautomers, metabolites, isotopologues and prodrugs thereof.

16 Claims, No Drawings

(56) References Cited

U.S. PATENT DOCUMENTS

| | | |
|---|---|---|
| 2003/0036652 A1 | 2/2003 | Bakthavatchalam et al. |
| 2003/0162968 A1 | 8/2003 | Ciriillo et al. |
| 2004/0023921 A1 | 2/2004 | Hong et al. |
| 2004/0063658 A1 | 4/2004 | Roberts et al. |
| 2004/0097485 A1 | 5/2004 | Burkitt et al. |
| 2004/0213757 A1 | 10/2004 | Zhu et al. |
| 2005/0009737 A1 | 1/2005 | Clark |
| 2006/0004014 A1 | 1/2006 | Hoffmann et al. |
| 2006/0106022 A1 | 5/2006 | Liu et al. |
| 2006/0135511 A1 | 6/2006 | Burgey |
| 2006/0142269 A1 | 6/2006 | Dykes |
| 2007/0280928 A1 | 12/2007 | Buck et al. |
| 2008/0214580 A1 | 9/2008 | Neagu et al. |
| 2009/0069289 A1 | 3/2009 | Neagu et al. |
| 2009/0163545 A1 | 6/2009 | Goldfard |
| 2009/0281075 A1 | 11/2009 | Roughton et al. |
| 2010/0144738 A1 | 6/2010 | Bornmann et al. |
| 2010/0249122 A1 | 9/2010 | Kalman |
| 2011/0137028 A1 | 6/2011 | Harris et al. |
| 2011/0257167 A1 | 10/2011 | Chopra et al. |
| 2012/0028972 A1 | 2/2012 | Wong |
| 2012/0059164 A1 | 3/2012 | Perrin-Ninkovic et al. |
| 2012/0071658 A1 | 3/2012 | Perrin-Ninkovic et al. |
| 2013/0225518 A1 | 8/2013 | Xu et al. |
| 2013/0245026 A1 | 9/2013 | Xu et al. |
| 2013/0245027 A1 | 9/2013 | Xu et al. |
| 2013/0245028 A1 | 9/2013 | Xu et al. |
| 2013/0245029 A1 | 9/2013 | Xu et al. |
| 2014/0113904 A1 | 4/2014 | Mortensen et al. |
| 2014/0113905 A1 | 4/2014 | Xu et al. |
| 2014/0314673 A1 | 10/2014 | Raymon et al. |
| 2014/0314674 A1 | 10/2014 | Raymon et al. |
| 2014/0314751 A1 | 10/2014 | Hege et al. |
| 2014/0314752 A1 | 10/2014 | Lopez-Girona et al. |
| 2014/0314753 A1 | 10/2014 | Hege et al. |
| 2014/0315848 A1 | 10/2014 | Raymon et al. |
| 2014/0315900 A1 | 10/2014 | Raymon et al. |
| 2014/0315907 A1 | 10/2014 | Raymon et al. |
| 2015/0099754 A1 | 4/2015 | Xu et al. |
| 2015/0174128 A1* | 6/2015 | Tester et al. ................ 514/249 |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/050076 | 5/2006 |
| WO | WO 2006/065703 | 6/2006 |
| WO | WO 2006/087530 | 8/2006 |
| WO | WO 2006/091737 | 8/2006 |
| WO | WO 2006/108103 | 10/2006 |
| WO | WO 2007/143212 | 12/2007 |
| WO | WO 2008/016669 | 2/2008 |
| WO | WO 2008/051493 | 5/2008 |
| WO | WO 2008/051494 | 5/2008 |
| WO | WO 2009/008992 | 1/2009 |
| WO | WO 2010/062571 | 6/2010 |
| WO | WO 2010/068483 | 6/2010 |
| WO | WO 2010/093435 | 8/2010 |
| WO | WO 2011/097333 | 8/2011 |

OTHER PUBLICATIONS

U.S. Appl. No. 13/654,441, filed Oct. 18, 2012, Xu et al.
U.S. Appl. No. 13/689,972, filed Nov. 30, 2012, Assaf et al.
U.S. Appl. No. 13/701,224, filed Mar. 5, 2013, Ning et al.
Barlin, "Purine analogs as amplifiers of phleomycin. VII. Some 1H-inidazo[4,5-b]pyrazines and related compound," Australian Journal of Chemistry, vol. 35, pp. 2299-2306 (1982).
Beresnev et al., "Interaction of 5-methoxy-1,2,4-traizines with uras as a new route to 6-azapurines," Medeleev Commu., vol. 2, pp. 58-59 (2000).
Bergmann et al., "2-Phenylpurines, their chemical and enzumological reactivity," J. Chem Org., pp. 3729-3735 (1963).
Booth et al., "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. pp. 2119-2126 (1992).
Booth et al., "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675 (1995).
Booth et al., "The Reactions of Diaminomaleonitrile with Isocyanates and Either Aldehydes or Ketones Revisited," J. Org Chem, vol. 66, pp. 8436-8441 (2001).
Booth, et al., "Synthesis of 4- and 5-Disubstituted 1-Benzylimidazoles, Important Precursors of Purine Analogs," J. of Heterocyclic of Chemistry, vol. 31(2), pp. 345-350 (1994).
Chupakhin et al., "A simple one pot synthesis of condensed 1,2,4-triazines by using the tandem $A_N$-$S_N$ipso and $S_N^H$—$S_N$ipso reactions," J. of Heterocyclic Chemistry, vol. 38(4), pp. 901-907 (2001).
Cohen, "The role of protein phosphorylation in human health and disease," Eur. J. Biochem, vol. 268, pp. 5001-5010 (2001).
Cohen, P. "Protein kinases—the major drug targets of the twenty-first century?" Nature Reviews/Drug Discovery, vol. 1, pp. 309-315 (2002).
Coish, et al., "Small molecule inhibitors of IKK kinase activity," Expert Opin. Ther. Patents, vol. 16(1), pp. 1-12 (2006).
Costa et al., "Aspects of mTOR biology and the use of mTOR inhibitors in non-Hodgkin's lymphoma," Cancer Treatment Reviews, Saunders, US, vol. 33(1), pp. 78-84 (2007).
Crofts et al., "Metabolism of 2-amino-1-methyl-6-phenylimidazo[4,5-b]pyridine (PhIP) by human cytochrome P4501B1," Carcinogenesis, vol. 18(9), pp. 1793-1798 (1997).
Dang et al., "Efficient synthesis of purines and purine nucelosides via an inverse electron demand diels—alder reaction," J. Am Chem Soc., vol. 121(24), pp. 5833-5834 (1999).
Database CAPLUS Online Chemical Abstracts Service, Columbus, Ohio, Database Accession No. 1951:49974 (XP-002472261) (1951).
Database CAPLUS Online Chemical Abstracts Service, Columbus, Ohio, Database Accession No. 1978:433195 (XP-002472262) (1978).
Database CAPLUS Online Chemical Abstracts Service, Columbus, Ohio, Database Accession No. 1966:26849 (XP-002472263) (1965).
Dornow et al., "Synthese von2-Oxy-imidazolo-(5',4':2,3)-pyridinen)," Arch Pharm. vol. 290, pp. 20-31 (1957) (w/English language abstract).
Dorwald F. Zaragoza, "Side Reactions in Organic Synthesis: A Guide to Successful Synthesis Design," Weinheim: Wiley-VCH Verlag GmbH & Co. KgaA, Preface. (2005).
Dzierba et al., "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23), pp. 5783-5790 (2004).
EPO Supplementary European Search Report dated Feb. 8, 2013 issued in connection with PCT/US2010/053678.

(56) References Cited

OTHER PUBLICATIONS

Fabbro et al., "Protein kinases as targets for anticancer agents: from inhibitors touseful drugs," Pharmacology & Therapeutics, vol. 93, pp. 79-98 (2002).
Farhadi et al., "The role of protein kinase C isoforms in modulating injury and repair of the intestinal barrier," J. Pharm Exp. Ther., vol. 316(1), pp. 1-7 (2006).
Frandsen et al., "Reaction of the N2-acetoxy derivative of 2-amino-1-methyl-6-phenylimidazo[4,5,b]pyridine . . . ," Carcinogenesis, vol. 13(4), pp. 629-635 (1992).
Frost et al., "AKT activity regulates the ability of mTOR inhibitors to prevent angiogenesis and VEGF expression in multiple myeloma cells," Oncogene, vol. 26(16), pp. 2255-2262 (2007).
Georgakis and Younes, "From rapi nui to rapamycin: targeting PI3K/Akt/mTOR for cancer therapy," Expert Rev. Anticancer Ther., vol. 6(1), 131-140 (2006).
Hamad, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4), pp. 939-944 (2001).
http://www.sigmaaldrich.com/catalog/product/ALDRICH/678740?lang=en&region=US, last accessed Nov. 1, 2012.
http://www.sigmaaldrich.com/catalog/product/ALDRICH/701602?lang=en&region=US#, last accessed Nov. 1, 2012.
http:/lwww.sigmaaldrich.com/catalog/product/aldrich/697230?lang=en&region=US, last accessed Nov. 1, 2012.
http:/lwww.sigmaaldrich.com/chemistry/chemical-synthesis/technology-spotlights/catalysisapplicationguide.html, last accessed Nov. 1, 2012.
Irie et al., "Toward the development of new medicinal leads with selectivity for protein kinase C isozymes," The Chemical Record, vol. 5, pp. 185-195 (2005).
Itoh et al., "A novel practical synthesis of C-2-arylpurines," Advanced Synthesis & Catalysis, vol. 346, pp. 1859-1867 (2004).
Gulati et al. "Involvement of mTORC1 and mTORC2 in regulation of glioblastoma multiforme growth and motility," International Journal of Oncology, vol. 35(4) (2009), abstract.
Jones et al., "6-Substituted-5-chloro-1,3-dihydro-2H-imidazo(4,5-b)pyrazin-2-ones with hypotensive activity," J. Med. Chem., vol. 16(5), pp. 537-542 (1973).
Jordan, V.C., Nature Reviews: Drug Discover, vol. 2, p. 205 (2003).
Kazaoka et al., "Synthesis of 6-substituted 9-benzyl-8-hydroxypurines with potential interferon-indcuing activity," Chemical & Pharmaceutical Bulletin, vol. 51(5), pp. 608-611 (2003).
Killday et al., "Microxine, a new cdc2 kinase inhibitor from the Australian marine sponge *Microxina* species," J. of Natural Products, vol. 64(4), pp. 525-526 (2001).
Minehan et al., "Molecular recognition of DNA by Hoechst Benzimidazoles: Exploring beyond theopyrrole-imidazole-hydroxypyrrole polyamide-pairing code," Helvitica Chima Acta, vol. 83(9), pp. 2197-2213 (2000).
Mortensen et al., "Discovery and SAR exploration of a novel series of imidazo[4,5-] pyrazin-2-ones as potent and selective mTOR kinase inhibitors," Bioorganic & Medicinal Chemistry Letters, Pergamon, Elsevier Science, GB, vol. 21(22), pp. 6793-6799 (2011).
Nagashima et al., "Solution-Phase parallel synthesis of an N-Alkylated dihydropteridinone library from fluorous amino acids," J of Comb. Chemistry, vol. 6(6), pp. 942-949 (2004).
Park et al., "A novel mechanism of TRAF signaling revealed by structural and functional analyses of the TRADD-TRAF2 interaction," Cell, vol. 101, pp. 777-787 (2000).
Patani et al., "Bioisosterim: A rational approach in drug design," Chemical Reviews, vol. 96, pp. 3147-3176 (1996).
Registry File Document for RN 863501-03-5, 863502-39-0 (Sep. 20, 2005).
Seela et al., "Product Class 17: Purines," Science of Synthesis, vol. 16, pp. 945-1108 (2004).
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Sridhar et al., "Protein Kinasesas Therapeutic Targets," Pharm. Research, vol. 17(11), pp. 1345-1353 (2000).
Office Action mailed Jun. 11, 2009 for U.S. Appl. No. 11/975,652.
Office Action mailed Sep. 2, 2009 for U.S. Appl. No. 11/975,652.
Final Office Action mailed Feb. 2, 2010 for U.S. Appl. No. 11/975,652 with Notice of References Cited.
Office Action mailed May 12, 2010 for U.S. Appl. No. 11/975,652.
Final Office Action mailed Sep. 30, 2010 for U.S. Appl. No. 11/975,652 with Notice of References Cited.
PCT International Search Report dated Mar. 29, 2010 issued in connection with PCT/US2009/062143.
PCT Written Opinion of the International Searching Authority dated Mar. 29, 2010.
Office Action mailed Nov. 10, 2010 for U.S. Appl. No. 12/605,791.
PCT IPRP with Written Opinion of the International Searching Authority dated May 12, 2011 in connection with PCT/US2009/062143.
Office Action mailed Jan. 19, 2011 for U.S. Appl. No. 12/605,791 with Notice of References Cited.
Final Office Action mailed May 10, 2011 for U.S. Appl. No. 12/605,791.
Advisory Action mailed Aug. 17, 2011 for U.S. Appl. No. 12/605,791.
Advisory Action mailed Sep. 14, 2011 for U.S. Appl. No. 2/605,791.
PCT International Search Report dated Dec. 27, 2010 issued in connection with PCT/US2010/053678.
PCT Written Opinion dated Dec. 27, 2010 in connection with PCT/US/10/53678.
Office Action mailed Feb. 28, 2012 for U.S. Appl. No. 12/910,920 with Notice of Reference Cited.
PCT IPRP dated May 10, 2012 issued in connection with PCT/US2010/053678.
Office Action mailed Jun. 28, 2012 for U.S. Appl. No. 12/910,920 with Notice of Reference Cited.
Final Office Action mailed Nov. 6, 2012 for U.S. Appl. No. 12/910,920 with Notice of Reference Cited.
Office Action mailed Apr. 2, 2012 for U.S. Appl. No. 13/295,513.
Office Action mailed Aug. 27, 2012 for U.S. Appl. No. 13/295,513 with Notice of References Cited.
PCT Partial International Search dated Feb. 21, 2013 issued in connection with PCT/US2012/060723.
PCT International Search Report dated Feb. 13, 2013 issued in connection with PCT/US2012/067172.
PCT Written Opinion dated Feb. 13, 2013 issued in connection with PCT/US/2012/067172.
Vippagunta et al., Advanced Drug Delivery Reviews, vol. 48, pp. 3-26 (2001) (Cited in Office Action in connection with U.S. Appl. No. 12/605,791).
Wallace, "Palladium-catalyzed synthesis of quinoxaline derivatives," Tetrahedron, vol. 64, pp. 9675-9684 (2008).
Westover et al., "Synthesis and antiviral activity of certain 9-β-D-Riofuranoaylpurine-6-carboxamides," J.Med. Chem., vol. 24(8), pp. 941-46 (1981).
Wolff, Manfred E., Ed. Burger's Medicinal Chemistry and Drug Discovery—Fifth Edition, New York: John Wiley & Sons, vol. 1, pp. 975-976 (1996).
Yoneda et al., "A transformation of 7-azapteridines into 6-azapurines (Imidazo[4,5-e]-as-triazines)," Heterocycles, vol. 4(9), pp. 1503-1508 (1976).
Yoneda et al., "Synthesis of imadazo[4,5-e]-as-triazine (6-Azapurine) Deriviatives," Chem & Pharm Bulletin, vol. 26(10), pp. 3154-3160 (1978).
Zaki et al., "The synthesis of imidazol[4,5-d]pyridines from a substituted imidazole and acyl or sulfonyl acetonitrile," Tetrahedron, vol. 63(18), pp. 3745-3753 (2007).
PCT Partial International Search dated Nov. 15, 2012 issued in connection with PCT/US2012/049281.
PCT International Search Report dated Jan. 11, 2013 issued in connection with PCT/US2012/049281.

(56) References Cited

OTHER PUBLICATIONS

PCT Written Opinion dated Feb. 13, 2013 issued in connection with PCT/US2012/049281.
Barr et al., "Erlotinib, an EGFR kinase inhibitor, sensitizes mesenchymal-like tumor cells to the actions of OXA-01, a selective non-macrolide inhibitor of mTORC1/mTORC2," European Journal of Cancer, Supplement, vol. 6, No. 12, pp. 103-104, Poster 325 (2008).
Bjornsti and Houghton, 2004, The TOR pathway: a target for cancer therapy. Nat Rev Cancer. 4(5):335-48.
Blanco et al., 2009,. "A gene-alteration profile of human lung cancer cell lines." Hum Mutat. 30(8):1199-206.
Buck et al., "Rapamycin synergizes with the epidermal growth factor receptor inhibitor erlotinib in non-small-cell lung, pancreatic, colon, and breast tumors," Molecular Cancer Therapeutics, vol. 5, No. 11, pp. 2676-2684 (2006).
Carretero et al., "Integrative Genomic and Proteomic Analyses Identify Targets for Lkb1-Deficient Metastatic Lung Tumors," Cancer Cell, vol. 17( 6), pp. 547-559 (2010).
Gao et al., "LKB1 in lung cancerigenesis: a serine/threonine kinase as tumor suppressor," Protein & Cell, vol. 2(2), pp. 99-107 (2011).
Gao et al., "LKB1 inhibits lung cancer progression through lysyl oxidase and extracellular matrix remodeling," Proceedings of the National Academy of Sciences, vol. 107(44), pp. 18892-18897 (2010).
Huang et al., "Genetic and epigenetic silencing of SCARA5 may contribute to human hepatocellular carcinoma by activating FAK signaling," Journal of Clinical Investigation, vol. 120(1), pp. 223-241 (2010).
Inge et al., "Expression of LKB1 tumor suppressor in non-small cell lung cancer determines sensitivity to 2-deoxyglucose," Journal of Thoracic and Cardiovascular Surgery, vol. 137(3), pp. 580-58 (2009).
Mahesh et al., 2010, Intratracheally administered 5-azacytidine is effective against orthotopic human lung cancer xenograft models and devoid of important systemic toxicity. Clin Lung Cancer. 11(6):405-11.
Nishino et al., 2010, "New Response Evaluation Criteria in Solid Tumors (RECIST) guidelines for advanced non-small cell lung cancer: comparison with original RECIST and impact on assessment of tumor response to targeted therapy." AJR Am J Roentgenol. 195(3):W221-8.
Papadimitrakopoulou et al., "A phase 1 / 2 study investigating the combination of RAD001® (everolimus) and erlotinib (E) as $2^{nd}$ and $3^{rd}$ line therapy in patients (pts) with advanced non-small cell lung cancer (NSCLC) previously treated with chemotherapy (C): Phase 1 results," Journal of Clinical Oncology, ASCO Annual Meeting Proceedings (Post-Meeting Edition), vol. 26, No. 15S, p. 8051 (2008).
Pérez-Soler et al., 2004, Determinants of tumor response and survival with erlotinib in patients with non-small-cell lung cancer. J Clin Oncol. 22(16):3238-47.
Shaw et al., "The LKB1 tumor suppressor negatively regulates mTOR signaling," Cancer Cell, vol. 6(1), pp. 91-99 (2004).
Wingo et al., "Somatic LKB1 Mutations Promote Cervical Cancer Progression," Plos One, vol. 4(4), pp. 5137-5138 (2009).
Yuan et al., "Targeting tumorigenesis: development and use of mTOR inhibitors in cancer therapy," Journal of Hematology & Oncology, vol. 2(1), p. 45 (2009).

\* cited by examiner

METHODS FOR TREATING CANCER USING TOR KINASE INHIBITOR COMBINATION THERAPY COMPRISING ADMINISTERING SUBSTITUTED PYRAZINO[2,3-B]PYRAZINES

This application claims the benefit of U.S. Provisional Application No. 61/980,124, filed Apr. 16, 2014, the entire contents of which are incorporated herein by reference.

1. FIELD

Provided herein are methods for treating or preventing a cancer comprising administering an effective amount of a TOR kinase inhibitor and an effective amount of a second active agent to a patient having a cancer.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001), *Protein Kinase Inhibitors for the Treatment of Disease: The Promise and the Problems*, Handbook of Experimental Pharmacology, Springer Berlin Heidelberg, 167 (2005).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7): 777-787 (2000).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/ PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. There remains a need for TOR kinase inhibitors that inhibit both mTORC1 and mTORC2 complexes.

DNA-dependent protein kinase (DNA-PK) is a serine/ threonine kinase involved in the repair of DNA double strand breaks (DSBs). DSBs are considered to be the most lethal DNA lesion and occur endogenously or in response to ionizing radiation and chemotherapeutics (for review see Jackson, S. P., Bartek, J. The DNA-damage response in human biology and disease. Nature Rev 2009; 461:1071-1078). If left unrepaired, DSBs will lead to cell cycle arrest and/or cell death (Hoeijmakers, J. H. J. Genome maintenance mechanisms for preventing cancer. Nature 2001; 411: 366-374; van Gent, D. C., Hoeijmakers, J. H., Kanaar, R. Chromosomal stability and the DNA double-stranded break connection. *Nat Rev Genet* 2001; 2: 196-206). In response to the insult, cells have developed complex mechanisms to repair such breaks and these mechanisms may form the basis of therapeutic resistance. There are two major pathways used to repair DSBs, non-homologous end joining (NHEJ) and homologous recombination (HR). NHEJ brings broken ends of the DNA together and rejoins them without reference to a second template (Collis, S. J., DeWeese, T. L., Jeggo P. A., Parker, A. R. The life and death of DNA-PK. Oncogene 2005; 24: 949-961). In contrast, HR is dependent on the proximity of the sister chromatid which provides a template to mediate faithful repair (Takata, M., Sasaki, M. S., Sonoda, E., Morrison, C., Hashimoto, M., Utsumi, H., et al. Homologous recombination and non-homologous end joining pathways of DNA double-strand break repair have overlapping roles in the maintenance of chromosomal integrity in vertebrate cells. *EMBO J* 1998; 17: 5497-5508; Haber, J. E. Partners and pathways repairing a double-strand break. *Trends Genet* 2000; 16: 259-264). NHEJ repairs the majority of DSBs. In NHEJ, DSBs are recognized by the Ku protein that binds and then activates the catalytic subunit of DNA-PK. This leads to recruitment and activation of end-processing enzymes, polymerases and DNA ligase IV (Collis, S. J., DeWeese, T. L., Jeggo P. A., Parker, A. R. The life and death of DNA-PK. *Oncogene* 2005; 24: 949-961). NHEJ is primarily controlled by DNA-PK and thus inhibition of DNA-PK is an attractive approach to modulating the repair response to exogenously induced DSBs. Cells deficient in components of the NHEJ pathway are defective in DSB repair and highly sensitive to ionizing radiation and topoisomerase poisons (reviewed by Smith, G. C. M., Jackson, S. P. The DNA-dependent protein kinase. *Genes Dev* 1999; 13: 916-934; Jeggo, P. A., Caldecott, K., Pidsley, S., Banks, G. R. Sensitivity of Chinese hamster ovary mutants defective in DNA double strand break repair to topoisomerase II inhibitors. *Cancer Res* 1989; 49: 7057-7063). A DNA-PK inhibitor has been reported to have the same effect of sensitizing cancer cells to therapeutically induced DSBs (Smith, G. C. M., Jackson, S. P. The DNA-dependent protein kinase. *Genes Dev* 1999; 13: 916-934).

Citation or identification of any reference in Section 2 of this application is not to be construed as an admission that the reference is prior art to the present application.

3. SUMMARY

Provided herein are methods for treating or preventing a cancer. A TOR kinase inhibitor is provided herein that can be used in the methods for treating or preventing a cancer. The methods comprise administering an effective amount of the TOR kinase inhibitor and an effective amount of a second active agent to a patient having a cancer.

In one embodiment, the second active agent is a receptor tyrosine kinase (RTK) inhibitor, a phosphoinositide 3-kinase (PI3K) pathway inhibitor, a serine/threonine-protein kinase (RAF) and mitogen-activated protein kinase/extracellular signal-regulated protein kinase kinase (MEK) pathway inhibitor, a DNA damaging agent, a DNA damage response agent, a cytoskeleton perturbagen, a protein stability inhibitor, or a Bruton's tyrosine kinase (BTK) inhibitor.

In certain embodiments, provided herein are methods for achieving an International Workshop on Chronic Lymphocytic Leukemia (IWCLL) response definition of complete response (CR), complete response with incomplete marrow recovery (CRi), partial response (PR), or stable disease (SD) in a patient having chronic lymphocytic leukemia, comprising administering an effective amount of a TOR kinase inhibitor in combination with a second active agent to said patient. The TOR kinase inhibitor provided herein can be used in the methods for achieving an International Workshop on Chronic Lymphocytic Leukemia (IWCLL) response definition of complete response (CR), complete response with incomplete marrow recovery (CRi), partial response (PR), or stable disease (SD) in a patient having chronic lymphocytic leukemia. In certain embodiments, provided herein are methods for achieving a National Cancer Institute-sponsored Working Group on Chronic Lymphocytic Leukemia (NCI-WG CLL) response definition of complete response (CR), complete response with incomplete marrow recovery (CRi), partial response (PR) or stable disease (SD) in a patient having chronic lymphocytic leukemia, comprising administering an effective amount of a TOR kinase inhibitor in combination with a second active agent to said patient. The TOR kinase inhibitor provided herein can be used in the methods for achieving a National Cancer Institute-sponsored Working Group on Chronic Lymphocytic Leukemia (NCI-WG CLL) response definition of complete response (CR), complete response with incomplete marrow recovery (CRi), partial response (PR) or stable disease (SD) in a patient having chronic lymphocytic leukemia. In certain embodiments, provided herein are methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with a second active agent to said patient. The TOR kinase inhibitor provided herein can be used in the methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with a second active agent to said patient. In certain embodiments, provided herein are methods for achieving an International Uniform Response Criteria (IURC) for multiple myeloma of complete response, partial response or stable disease in a patient having multiple myeloma, comprising administering an effective amount of a TOR kinase inhibitor in combination with a second active agent to said patient. The TOR kinase inhibitor provided herein can be used in the methods for achieving an International Uniform Response Criteria (IURC) for multiple myeloma of complete response, partial response or stable disease in a patient having multiple myeloma. In certain embodiments, provided herein are methods for achieving a Response Evaluation Criteria in Solid Tumors (for example, RECIST 1.1) of complete response, partial response or stable disease in a patient having a solid tumor, comprising administering an effective amount of a TOR kinase inhibitor in combination with a second active agent to said patient. The TOR kinase inhibitor provided herein can be used in the methods for achieving a Response Evaluation Criteria in Solid Tumors (for example, RECIST 1.1) of complete response, partial response or stable disease in a patient having a solid tumor. In certain embodiments, provided herein are methods for achieving a Prostate Cancer Working Group 2 (PCWG2) Criteria of complete response, partial response or stable disease in a patient having prostate cancer, comprising administering an effective amount of a TOR kinase inhibitor in combination with a second active agent to said patient. The TOR kinase inhibitor provided herein can be used in the methods for achieving a Prostate Cancer Working Group 2 (PCWG2) Criteria of complete response, partial response or stable disease in a patient having prostate cancer. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering an effective amount of a TOR kinase inhibitor in combination with a second active agent to said patient. The TOR kinase inhibitor provided herein can be used in the methods for achieving a Responses Assessment for Neuro-Oncology (RANO) Working Group for glioblastoma multiforme of complete response, partial response or stable disease in a patient having glioblastoma multiforme.

In certain embodiments, provided herein are methods for increasing survival without cancer progression of a patient having a cancer, comprising administering an effective amount of a TOR kinase inhibitor in combination with an effective amount of a second active agent. The TOR kinase inhibitor provided herein can be used in the methods for increasing survival without cancer progression of a patient having a cancer.

In certain embodiments, the TOR kinase inhibitor is a compound as described herein.

The present embodiments can be understood more fully by reference to the detailed description and examples, which are intended to exemplify non-limiting embodiments.

4. DETAILED DESCRIPTION

4.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturared alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyrdine-3-yl methyl, (tetrahydro-2H-pyran-4-yl)methyl, (tetrahydro-2H-pyran-4-yl)ethyl, tetrahydrofuran-2-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —$NH_2$.

A "hydroxyl amine" group is a radical of the formula: —N($R^\#$)OH or —NHOH, wherein $R^\#$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N($R^\#$)O-alkyl or —NHO-alkyl, wherein $R^\#$ is as defined above.

An "aralkoxyamine" group is a radical of the formula: —N($R^\#$)O-aryl or —NHO-aryl, wherein $R^\#$ is as defined above.

An "alkylamine" group is a radical of the formula: —NH-alkyl or —N(alkyl)$_2$, wherein each alkyl is independently as defined above.

An "aminocarbonyl" group is a radical of the formula: —C(=O)N($R^\#$)$_2$, —C(=O)NH($R^\#$) or —C(=O)$NH_2$, wherein each $R^\#$ is as defined above.

An "acylamino" group is a radical of the formula: —NHC(=O)($R^\#$) or —N(alkyl)C(=O)($R^\#$), wherein each alkyl and $R^\#$ are independently as defined above.

An "O(alkyl)aminocarbonyl" group is a radical of the formula: —O(alkyl)C(=O)N($R^\#$)$_2$, —O(alkyl)C(=O)NH($R^\#$) or —O(alkyl)C(=O)$NH_2$, wherein each $R^\#$ is independently as defined above.

An "N-oxide" group is a radical of the formula: —$N^+$—$O^-$.

A "carboxy" group is a radical of the formula: —C(=O)OH.

A "ketone" group is a radical of the formula: —C(=O)($R^\#$), wherein $R^\#$ is as defined above.

An "aldehyde" group is a radical of the formula: —CH(=O).

An "ester" group is a radical of the formula: —C(=O)O($R^\#$) or —OC(=O)($R^\#$), wherein $R^\#$ is as defined above.

A "urea" group is a radical of the formula: —N(alkyl)C(=O)N($R^\#$)$_2$, —N(alkyl)C(=O)NH($R^\#$), —N(alkyl)C(=O)$NH_2$, —NHC(=O)N($R^\#$)$_2$, —NHC(=O)NH($R^\#$), or —NHC(=O)$NH_2^\#$, wherein each alkyl and $R^\#$ are independently as defined above.

An "imine" group is a radical of the formula: —N=C($R^\#$)$_2$ or —C($R^\#$)=N($R^\#$), wherein each $R^\#$ is independently as defined above.

An "imide" group is a radical of the formula: —C(=O)N(R#)C(=O)($R^\#$) or —N((C=O)($R^\#$))$_2$, wherein each $R^\#$ is independently as defined above.

A "urethane" group is a radical of the formula: —OC(=O)N($R^\#$)$_2$, —OC(=O)NH($R^\#$), —N($R^\#$)C(=O)O($R^\#$), or —NHC(=O)O($R^\#$), wherein each $R^\#$ is independently as defined above.

An "amidine" group is a radical of the formula: —C(=N($R^\#$))N($R^\#$)$_2$, —C(=N($R^\#$))NH($R^\#$), —C(=N($R^\#$))$NH_2$, —C(=NH)N($R^\#$)$_2$, —C(=NH)NH($R^\#$), —C(=NH)$NH_2$, —N=C($R^\#$)N($R^\#$)$_2$, —N=C($R^\#$)NH($R^\#$), —N=C($R^\#$)$NH_2$, —N($R^\#$)C($R^\#$)=N($R^\#$), —NHC($R^\#$)=N($R^\#$), —N($R^\#$)C($R^\#$)=NH, or —NHC($R^\#$)=NH, wherein each $R^\#$ is independently as defined above.

A "guanidine" group is a radical of the formula: —N($R^\#$)C(=N($R^\#$))N($R^\#$)$_2$, —NHC(=N($R^\#$))N($R^\#$)$_2$, —N($R^\#$)C(=NH)N($R^\#$)$_2$, —N($R^\#$)C(=N($R^\#$))NH($R^\#$), —N($R^\#$)C(=N($R^\#$))$NH_2$, —NHC(=NH)N($R^\#$)$_2$, —NHC(=N($R^\#$))NH($R^\#$), —NHC(=N($R^\#$))$NH_2$, —NHC(=NH)NH($R^\#$), —NHC(=NH)$NH_2$, —N=C(N($R^\#$)$_2$)$_2$, —N=C(NH($R^\#$))$_2$, or —N=C($NH_2$)$_2$, wherein each $R^\#$ is independently as defined above.

An "enamine" group is a radical of the formula: —N($R^\#$)C($R^\#$)=C($R^\#$)$_2$, —NHC($R^\#$)=C($R^\#$)$_2$, —C(N($R^\#$)$_2$)=C($R^\#$)$_2$, —C(NH($R^\#$))=C($R^\#$)$_2$, —C($NH_2$)=C($R^\#$)$_2$, —C(R#)═C(R#)(N(R#)$_2$), —C(R#)═C(R#)(NH(R#)) or —C(R#)═C(R#)(NH$_2$), wherein each R# is independently as defined above.

An "oxime" group is a radical of the formula: —C(═NO(R#))(R#), —C(═NOH)(R#), —CH(═NO(R#)), or —CH(═NOH), wherein each R# is independently as defined above.

A "hydrazide" group is a radical of the formula: —C(═O)N(R#)N(R#)$_2$, —C(═O)NHN(R#)$_2$, —C(═O)N(R#)NH(R#), —C(═O)N(R#)NH$_2$, —C(═O)NHNH(R#)$_2$, or —C(═O)NHNH$_2$, wherein each R# is independently as defined above.

A "hydrazine" group is a radical of the formula: —N(R#)N(R#)$_2$, —NHN(R#)$_2$, —N(R#)NH(R#), —N(R#)NH$_2$, —NHNH(R#)$_2$, or —NHNH$_2$, wherein each R# is independently as defined above.

A "hydrazone" group is a radical of the formula: —C(═N—N(R#)$_2$)(R#)$_2$, —C(═N—NH(R#))(R#)$_2$, —C(═N—NH$_2$)(R#)$_2$, —N(R#)(N═C(R#)$_2$), or —NH(N═C(R#)$_2$), wherein each R# is independently as defined above.

An "azide" group is a radical of the formula: —N$_3$.

An "isocyanate" group is a radical of the formula: —N═C═O.

An "isothiocyanate" group is a radical of the formula: —N═C═S.

A "cyanate" group is a radical of the formula: —OCN.

A "thiocyanate" group is a radical of the formula: —SCN.

A "thioether" group is a radical of the formula; —S(R#), wherein R# is as defined above.

A "thiocarbonyl" group is a radical of the formula: —C(═S)(R#), wherein R# is as defined above.

A "sulfinyl" group is a radical of the formula: —S(═O)(R#), wherein R# is as defined above.

A "sulfone" group is a radical of the formula: —S(═O)$_2$(R#), wherein R# is as defined above.

A "sulfonylamino" group is a radical of the formula: —NHSO$_2$(R#) or —N(alkyl)SO$_2$(R#), wherein each alkyl and R# are defined above.

A "sulfonamide" group is a radical of the formula: —S(═O)$_2$N(R#)$_2$, or —S(═O)$_2$NH(R#), or —S(═O)$_2$NH$_2$, wherein each R# is independently as defined above.

A "phosphonate" group is a radical of the formula: —P(═O)(O(R#))$_2$, —P(═O)(OH)$_2$, —OP(═O)(O(R#))(R#), or —OP(═O)(OH)(R#), wherein each R# is independently as defined above.

A "phosphine" group is a radical of the formula: —P(R#)$_2$, wherein each R# is independently as defined above.

When the groups described herein, with the exception of alkyl group are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (═O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic or besylate, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a TOR kinase inhibitor, or a salt thereof, in the form of a crystal lattice that contains spaces (e.g., channels) that have a guest molecule (e.g., a solvent or water) trapped within or a crystal lattice wherein a TOR kinase inhibitor is a guest molecule.

As used herein and unless otherwise indicated, the term "solvate" means a TOR kinase inhibitor, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a TOR kinase inhibitor, or a salt thereof, that further includes a stoichiometric or non-stoichiometric amount of water bound by non-covalent intermolecular forces.

As used herein and unless otherwise indicated, the term "prodrug" means a TOR kinase inhibitor derivative that can hydrolyze, oxidize, or otherwise react under biological conditions (in vitro or in vivo) to provide an active compound, particularly a TOR kinase inhibitor. Examples of prodrugs include, but are not limited to, derivatives and metabolites of a TOR kinase inhibitor that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and

*Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a TOR kinase inhibitor that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The TOR kinase inhibitors can have chiral centers and can occur as racemates, individual enantiomers or diastereomers, and mixtures thereof. All such isomeric forms are included within the embodiments disclosed herein, including mixtures thereof. The use of stereomerically pure forms of such TOR kinase inhibitors, as well as the use of mixtures of those forms are encompassed by the embodiments disclosed herein. For example, mixtures comprising equal or unequal amounts of the enantiomers of a particular TOR kinase inhibitor may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the TOR kinase inhibitors can include E and Z isomers, or a mixture thereof, and cis and trans isomers or a mixture thereof. In certain embodiments, the TOR kinase inhibitors are isolated as either the cis or trans isomer. In other embodiments, the TOR kinase inhibitors are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

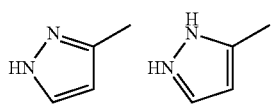

As readily understood by one skilled in the art, a wide variety of functional groups and other structures may exhibit tautomerism and all tautomers of the TOR kinase inhibitors are within the scope of the present invention.

It should also be noted the TOR kinase inhibitors can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the TOR kinase inhibitors as described herein, whether radioactive or not, are intended to be encompassed within the scope of the embodiments provided herein. In some embodiments, there are provided isotopologues of the TOR kinase inhibitors, for example, the isotopologues are deuterium, carbon-13, or nitrogen-15 enriched TOR kinase inhibitors.

It should be noted that if there is a discrepancy between a depicted structure and a name for that structure, the depicted structure is to be accorded more weight.

"Treating" as used herein, means an alleviation, in whole or in part, of a cancer or a symptom associated with a cancer, or slowing, or halting of further progression or worsening of those symptoms.

"Preventing" as used herein, means the prevention of the onset, recurrence or spread, in whole or in part, of a cancer, or a symptom thereof.

The term "effective amount" in connection with an TOR kinase inhibitor or a second active agent means an amount alone or in combination capable of alleviating, in whole or in part, a symptom associated with a cancer, or slowing or halting further progression or worsening of those symptoms, or treating or preventing a cancer in a subject having or at risk for having a cancer. The effective amount of the TOR kinase inhibitor or a second active agent, for example in a pharmaceutical composition, may be at a level that will exercise the desired effect; for example, about 0.005 mg/kg of a subject's body weight to about 100 mg/kg of a patient's body weight in unit dosage for both oral and parenteral administration.

The term "second active agent(s)" means a receptor tyrosine kinase (RTK) inhibitor (for example, an EGFR inhibitor), a phosphoinositide 3-kinase (PI3K) pathway inhibitor, a serine/threonine-protein kinase (RAF) and mitogen-activated protein kinase/extracellular signal-regulated protein kinase kinase (MEK) pathway inhibitor, a DNA damaging agent (for example, a PARP inhibitor), a DNA damage response agent, a cytoskeleton perturbagen, a protein stability inhibitor, or a Bruton's tyrosine kinase (BTK) inhibitor, including those described herein in Section 4.4.

"Combination" or administration "in combination" includes administration as a mixture, simultaneous administration using separate formulations, and consecutive administration in any order.

"Consecutive" means that more than 10 minutes have passed between the administration of the TOR kinase inhibitor and the administration of the second active agent. The time period can then be more than 10 min, more than 30 minutes, more than 1 hour, more than 3 hours, more than 6 hours or more than 12 hours.

The term "cancer" includes, but is not limited to, blood borne tumors and solid tumors. Blood borne tumors include lymphomas, leukemias and myelomas. Lymphomas and leukemias are malignancies arising among white blood cells.

The term "cancer" also refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

The term "refractory B-cell non-Hodgkin's lymphoma" as used herein is defined as B-cell non-Hodgkin's lymphoma which was treated with an anti-CD-20 antibody-containing regimen, for example rituximab-containing regimen, (i) without achieving at least a partial response to therapy or (ii) which progressed within 6 months of treatment.

The term "relapsed B-cell non-Hodgkin's lymphoma" as used herein is defined as B-cell non-Hodgkin's lymphoma which progressed after ≥6 months post-treatment with an anti-CD-20 antibody-containing regimen, for example rituximab-containing regimen, after achieving partial response or complete response to therapy.

A person of ordinary skill will appreciate that diseases characterized as "B-cell lymphoma" exist as a continuum of diseases or disorders. While the continuum of B-cell lymphomas is sometimes discussed in terms of "aggressive" B-cell lymphomas or "indolent" B-cell lymphomas, a person of ordinary skill will appreciate that a B-cell lymphoma characterized as indolent may progress and become an aggressive B-cell lymphoma. Conversely, an aggressive form of B-cell lymphoma may be downgraded to an indolent or stable form of B-cell lymphoma. Reference is made to indolent and aggressive B-cell lymphomas as generally understood by a person skilled in the art with the recognition that such characterizations are inherently dynamic and depend on the particular circumstances of the individual.

As used herein, and unless otherwise specified, the term "in combination with" includes the administration of two or more therapeutic agents simultaneously, concurrently, or sequentially within no specific time limits unless otherwise indicated. In one embodiment, a TOR kinase inhibitor is administered in combination with a second active agent. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, or any combination thereof. For example, in one embodiment, the first agent can be administered prior to the second therapeutic agent, for e.g. 1 week. In another, the first agent can be administered prior to (for example 1 day prior) and then concomitant with the second therapeutic agent.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having a cancer.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [$^{18}$F]fluorodeoxyglucose; PET, positron emission tomography; CT, computed tomography; PR, partial remission; SPD, sum of the product of the diameters; SD, stable disease; PD, progressive disease.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or >50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by≥90% or to <200 mg per 24 h If the serum and urine M-protein are unmeasurable,[d] a ≥50% decrease in the difference between involved and uninvolved FLC levels is required in place of the M-protein criteria If serum and urine M-protein are unmeasurable, and serum free light assay is also unmeasurable, ≥50% reduction in plasma cells is required in place of M-protein, provided baseline bone marrow plasma cell percentage was ≥30% In addition to the above listed criteria, if present at baseline, a ≥50% reduction in the size of soft tissue plasmacytomas is also required |

| Response Subcategory | Response Criteria[a] |
| --- | --- |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;

[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
| --- | --- | --- | --- |
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (i.e., less than 5 mm by 5 mm), nonenhancing lesions (e.g., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (e.g., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor. For example, the inhibition of phosphorylation of S6RP, 4E-BP1, AKT and/or DNA-PK is assessed in B-cells, T-cells and/or monocytes. In other embodiments, treatment of a cancer may be assessed by the inhibition of DNA-dependent protein kinase (DNA-PK) activity in skin samples and/or tumor biopsies/aspirates, such as by assessment of the amount of pDNA-PK 52056 as a biomarker for DNA damage pathways, before, during, and/or after TOR kinase inhibitor treatment. In one embodiment, the skin sample is irradiated by UV light.

In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

4.2 TOR Kinase Inhibitors

The compounds provided herein are generally referred to as "TOR kinase inhibitor(s)." In one aspect, the TOR kinase inhibitors do not include rapamycin or rapamycin analogs (rapalogs).

In one embodiment, the TOR kinase inhibitors include compounds having the following formula (I):

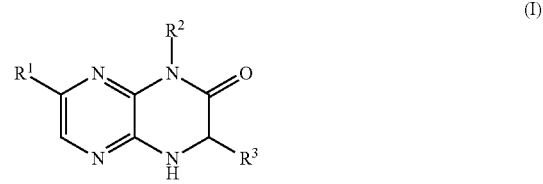

and pharmaceutically acceptable salts, clathrates, solvates, stereoisomers, tautomers, metabolites, isotopologues and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the TOR kinase inhibitors do not include 7-(4-hydroxyphenyl)-1-(3-methoxybenzyl)-3,4-dihydropyrazino[2,3-b]pyrazin-2(1H)-one, depicted below:

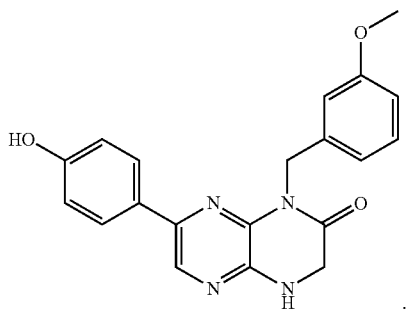 [SMILES: COc1cccc(CN2C(=O)CNc3ncc(-c4ccc(O)cc4)nc32)c1]

In some embodiments of compounds of formula (I), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

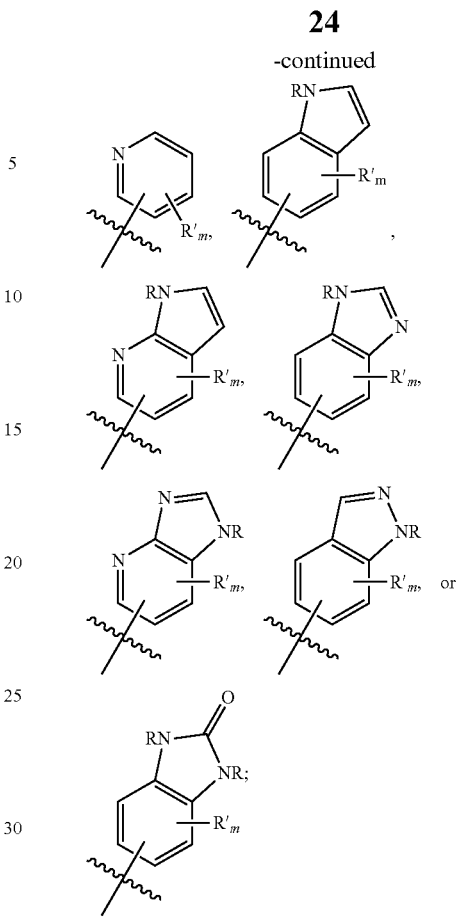

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —$NR_2$; m is 0-3; and n is 0-3. It will be understood by those skilled in the art that any of the substituents R' may be attached to any suitable atom of any of the rings in the fused ring systems.

In some embodiments of compounds of formula (I), $R^1$ is

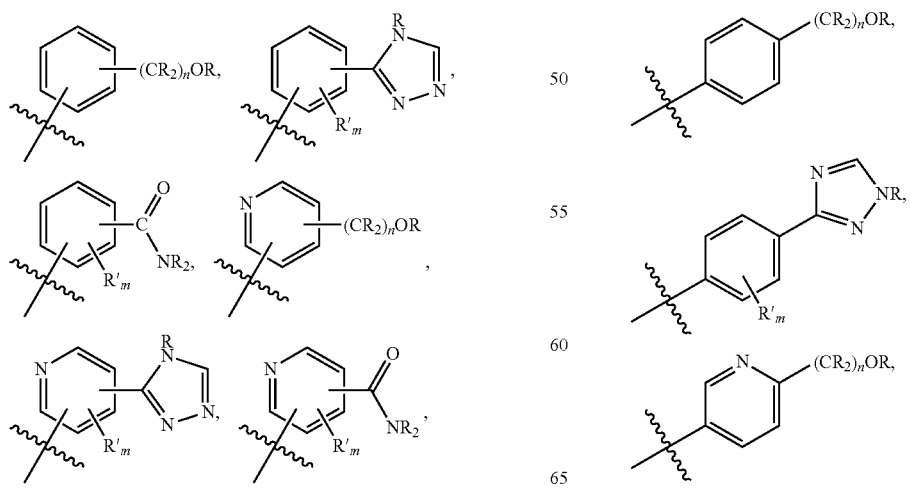

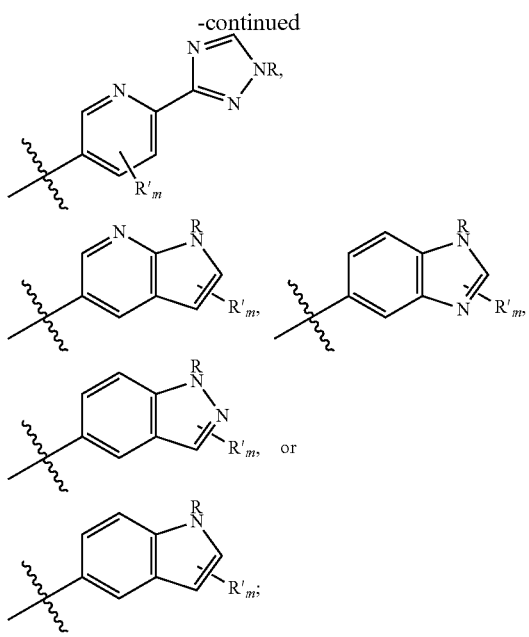

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —NR$_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

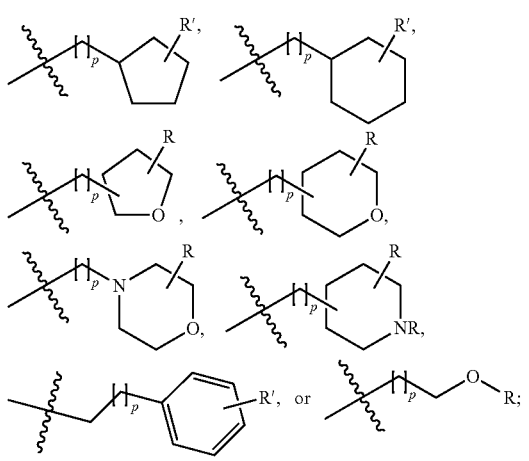

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (I), $R^2$ is H, $C_{1-4}$ alkyl, ($C_{1-4}$alkyl)(OR),

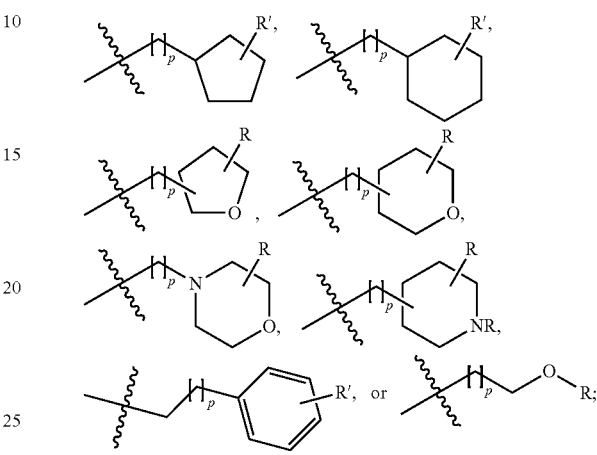

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (I), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —NR$_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —NR$_2$, wherein R is independently H, or a substituted or unsubstituted $C_{1-4}$ alkyl.

In certain embodiments, the compounds of formula (I) have an $R^1$ group set forth herein and an $R^2$ group set forth herein.

In some embodiments of compounds of formula (I), the compound inhibits TOR kinase. In other embodiments of compounds of formula (I), the compound inhibits DNA-PK. In certain embodiments of compounds of formula (I), the compound inhibits both TOR kinase and DNA-PK.

In some embodiments of compounds of formula (I), the compound at a concentration of 10 μM inhibits TOR kinase, DNA-PK, PI3K, or a combination thereof by at least about 50%. Compounds of formula (I) may be shown to be inhibitors of the kinases above in any suitable assay system.

Representative TOR kinase inhibitors of formula (I) include compounds from Table A.

TABLE A 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-methoxycyclohexyl)-3,4-dihydropyrazino[2,3-b]pyrazin-2(1H)-one;
7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;
1-ethyl-7-(1H-pyrrolo[3,2-b]pyridin-5-yl)-3,4-dihydropyrazino[2,3-b]pyrazin-2(1H)-one;
7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;
7-(1H-benzo[d]imidazol-4-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;
7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;
7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;
7-(6-(1H-1,2,4-triazol-3-yl)pyridin-3-yl)-1-(2-methoxyethyl)-3,4-dihydropyrazino[2,3-b]pyrazin-2(1H)-one;
7-(6-(1H-1,2,4-triazol-3-yl)pyridin-3-yl)-1-ethyl-3,4-dihydropyrazino[2,3-b]pyrazin-2(1H)-one;
7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;
7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;
7-(1H-indol-4-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(trans-4-hydroxycyclohexyl)-3,4-dihydropyrazino[2,3-b]pyrazin-2(1H)-one;
7-(6-(1H-1,2,4-triazol-3-yl)pyridin-3-yl)-1-(trans-4-methoxycyclohexyl)-3,4-dihydropyrazino[2,3-b]pyrazin-2(1H)-one;
7-(6-(1H-1,2,4-triazol-3-yl)pyridin-3-yl)-1-isopropyl-3,4-dihydropyrazino[2,3-b]pyrazin-2(1H)-one;
7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;
7-(5-fluoro-2-methyl-4-(1H-1,2,4-triazol-3-yl)phenyl)-1-isopropyl-3,4-dihydropyrazino[2,3-b]pyrazin-2(1H)-one;
1-ethyl-7-(5-fluoro-2-methyl-4-(1H-1,2,4-triazol-3-yl)phenyl)-3,4-dihydropyrazino[2,3-b]pyrazin-2(1H)-one;
7-(2-hydroxypyridin-4-yl)-1-(2-(tetrahydro-2H-pyran-4-yl)ethyl)-3,4-dihydropyrazino[2,3-b]pyrazin-2(1H)-one;
1-isopropyl-7-(4-methyl-6-(1H-1,2,4-triazol-3-yl)pyridin-3-yl)-3,4-dihydropyrazino[2,3-b]pyrazin-2(1H)-one;
5-(8-isopropyl-7-oxo-5,6,7,8-tetrahydropyrazino[2,3-b]pyrazin-2-yl)-4-methylpicolinamide;
7-(1H-indazol-4-yl)-1-(2-(tetrahydro-2H-pyran-4-yl)ethyl)-3,4-dihydropyrazino[2,3-b]pyrazin-2(1H)-one;
7-(2-aminopyrimidin-5-yl)-1-(2-(tetrahydro-2H-pyran-4-yl)ethyl)-3,4-dihydropyrazino[2,3-b]pyrazin-2(1H)-one;
7-(2-aminopyridin-4-yl)-1-(2-(tetrahydro-2H-pyran-4-yl)ethyl)-3,4-dihydropyrazino[2,3-b]pyrazin-2(1H)-one;
7-(6-(methylamino)pyridin-3-yl)-1-(2-(tetrahydro-2H-pyran-4-yl)ethyl)-3,4-dihydropyrazino[2,3-b]pyrazin-2(1H)-one;
7-(6-hydroxypyridin-3-yl)-1-(2-(tetrahydro-2H-pyran-4-yl)ethyl)-3,4-dihydropyrazino[2,3-b]pyrazin-2(1H)-one;
7-(4-(1H-pyrazol-3-yl)phenyl)-1-(2-methoxyethyl)-3,4-dihydropyrazino[2,3-b]pyrazin-2(1H)-one;
7-(pyridin-3-yl)-1-(2-(tetrahydro-2H-pyran-4-yl)ethyl)-3,4-dihydropyrazino[2,3-b]pyrazin-2(1H)-one;
7-(1H-indazol-4-yl)-1-(2-methoxyethyl)-3,4-dihydropyrazino[2,3-b]pyrazin-2(1H)-one;
7-(1H-indazol-6-yl)-1-(2-methoxyethyl)-3,4-dihydropyrazino[2,3-b]pyrazin-2(1H)-one;
7-(pyrimidin-5-yl)-1-(2-(tetrahydro-2H-pyran-4-yl)ethyl)-3,4-dihydropyrazino[2,3-b]pyrazin-2(1H)-one;

TABLE A-continued 7-(6-methoxypyridin-3-yl)-1-(2-(tetrahydro-2H-pyran-4-yl)ethyl)-3,4-dihydropyrazino[2,3-b]pyrazin-2(1H)-one;
1-(2-methoxyethyl)-7-(1H-pyrrolo[2,3-b]pyridin-5-yl)-3,4-dihydropyrazino[2,3-b]pyrazin-2(1H)-one;
1-ethyl-7-(1H-pyrrolo[2,3-b]pyridin-5-yl)-3,4-dihydropyrazino[2,3-b]pyrazin-2(1H)-one;
1-ethyl-7-(1H-indazol-4-yl)-3,4-dihydropyrazino[2,3-b]pyrazin-2(1H)-one;
7-(pyridin-4-yl)-1-(2-(tetrahydro-2H-pyran-4-yl)ethyl)-3,4-dihydropyrazino[2,3-b]pyrazin-2(1H)-one;
7-(6-aminopyridin-3-yl)-1-(2-(tetrahydro-2H-pyran-4-yl)ethyl)-3,4-dihydropyrazino[2,3-b]pyrazin-2(1H)-one;
1-methyl-7-(2-methyl-6-(4H-1,2,4-triazol-3-yl)pyridin-3-yl)-3,4-dihydropyrazino[2,3-b]pyrazin-2(1H)-one;
2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;
4-methyl-5-(7-oxo-8-((tetrahydro-2H-pyran-4-yl)methyl)-5,6,7,8-tetrahydropyrazino[2,3-b]pyrazin-2-yl)picolinamide;
5-(8-((cis-4-methoxycyclohexyl)methyl)-7-oxo-5,6,7,8-tetrahydropyrazino[2,3-b]pyrazin-2-yl)-4-methylpicolinamide;
7-(1H-pyrazol-4-yl)-1-(2-(tetrahydro-2H-pyran-4-yl)ethyl)-3,4-dihydropyrazino[2,3-b]pyrazin-2(1H)-one;
1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;
3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;
1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;
3-(7-oxo-8-(2-(tetrahydro-2H-pyran-4-yl)ethyl)-5,6,7,8-tetrahydropyrazino[2,3-b]pyrazin-2-yl)benzamide;
5-(8-((trans-4-methoxycyclohexyl)methyl)-7-oxo-5,6,7,8-tetrahydropyrazino[2,3-b]pyrazin-2-yl)-4-methylpicolinamide;
3-((7-(6-(2-hydroxypropan-2-yl)pyridin-3-yl)-2-oxo-3,4-dihydropyrazino[2,3-b]pyrazin-1(2H)-yl)methyl)benzonitrile;
7-(6-(2-hydroxypropan-2-yl)pyridin-3-yl)-1-((1R,3R)-3-methoxycyclopentyl)-3,4-dihydropyrazino[2,3-b]pyrazin-2(1H)-one;
7-(6-(2-hydroxypropan-2-yl)pyridin-3-yl)-1-((1S,3R)-3-methoxycyclopentyl)-3,4-dihydropyrazino[2,3-b]pyrazin-2(1H)-one;
7-(6-(2-hydroxypropan-2-yl)pyridin-3-yl)-1-((1S,3S)-3-methoxycyclopentyl)-3,4-dihydropyrazino[2,3-b]pyrazin-2(1H)-one;
7-(6-(2-hydroxypropan-2-yl)pyridin-3-yl)-1-((1R,3S)-3-methoxycyclopentyl)-3,4-dihydropyrazino[2,3-b]pyrazin-2(1H)-one;
7-(1H-indazol-6-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(2-morpholinoethyl)-3,4-dihydropyrazino[2,3-b]pyrazin-2(1H)-one;
1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(2-morpholinoethyl)-3,4-dihydropyrazino[2,3-b]pyrazin-2(1H)-one;
1-isopropyl-7-(2-methyl-6-(4H-1,2,4-triazol-3-yl)pyridin-3-yl)-3,4-dihydropyrazino[2,3-b]pyrazin-2(1H)-one;
7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;
1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
1-(trans-4-hydroxycyclohexyl)-7-(6-(2-hydroxypropan-2-yl)pyridin-3-yl)-3,4-dihydropyrazino[2,3-b]pyrazin-2(1H)-one;
1-(cis-4-hydroxycyclohexyl)-7-(6-(2-hydroxypropan-2-yl)pyridin-3-yl)-3,4-dihydropyrazino[2,3-b]pyrazin-2(1H)-one;
4-(7-oxo-8-(2-(tetrahydro-2H-pyran-4-yl)ethyl)-5,6,7,8-tetrahydropyrazino[2,3-b]pyrazin-2-yl)benzamide;
7-(1H-indazol-5-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;
1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
7-(1H-indol-5-yl)-1-(2-(tetrahydro-2H-pyran-4-yl)ethyl)-3,4-dihydropyrazino[2,3-b]pyrazin-2(1H)-one;
1-ethyl-7-(2-methyl-6-(4H-1,2,4-triazol-3-yl)pyridin-3-yl)-3,4-dihydropyrazino[2,3-b]pyrazin-2(1H)-one;

TABLE A-continued 7-(1H-indol-6-yl)-1-(2-(tetrahydro-2H-pyran-4-yl)ethyl)-3,4-dihydropyrazino[2,3-b]pyrazin-2(1H)-one;
7-(4-(2-hydroxypropan-2-yl)phenyl)-1-(trans-4-methoxycyclohexyl)-3,4-dihydropyrazino[2,3-b]pyrazin-2(1H)-one;
7-(6-(2-hydroxypropan-2-yl)pyridin-3-yl)-1-(tetrahydro-2H-pyran-4-yl)-3,4-dihydropyrazino[2,3-b]pyrazin-2(1H)-one;
1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((cis-4-methoxycyclohexyl)methyl)-3,4-dihydropyrazino[2,3-b]pyrazin-2(1H)-one;
1-(2-methoxyethyl)-7-(4-methyl-2-(methylamino)-1H-benzo[d]imidazol-6-yl)-3,4-dihydropyrazino[2,3-b]pyrazin-2(1H)-one;
7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;
7-(2-methyl-4-(4H-1,2,4-triazol-3-yl)phenyl)-3,4-dihydropyrazino[2,3-b]pyrazin-2(1H)-one;
1-(2-methoxyethyl)-7-(4-methyl-6-(1H-1,2,4-triazol-3-yl)pyridin-3-yl)-3,4-dihydropyrazino[2,3-b]pyrazin-2(1H)-one;
1-benzyl-7-(2-methyl-4-(4H-1,2,4-triazol-3-yl)phenyl)-3,4-dihydropyrazino[2,3-b]pyrazin-2(1H)-one;
7-(3-fluoro-4-(4H-1,2,4-triazol-3-yl)phenyl)-1-(2-methoxyethyl)-3,4-dihydropyrazino[2,3-b]pyrazin-2(1H)-one;
7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;
1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(trans-4-methoxycyclohexyl)-3,4-dihydropyrazino[2,3-b]pyrazin-2(1H)-one;
7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
1-(2-methoxyethyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((trans-4-methoxycyclohexyl)methyl)-3,4-dihydropyrazino[2,3-b]pyrazin-2(1H)-one;
1-(cyclopentylmethyl)-7-(6-(2-hydroxypropan-2-yl)pyridin-3-yl)-3,4-dihydropyrazino[2,3-b]pyrazin-2(1H)-one;
7-(4-(2-hydroxypropan-2-yl)phenyl)-1-(2-methoxyethyl)-3,4-dihydropyrazino[2,3-b]pyrazin-2(1H)-one;
(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;
7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(4-(trifluoromethyl)benzyl)-3,4-dihydropyrazino[2,3-b]pyrazin-2(1H)-one;
7-(6-(2-hydroxypropan-2-yl)pyridin-3-yl)-1-(3-(trifluoromethyl)benzyl)-3,4-dihydropyrazino[2,3-b]pyrazin-2(1H)-one;
7-(6-(2-hydroxypropan-2-yl)pyridin-3-yl)-1-(3-methoxypropyl)-3,4-dihydropyrazino[2,3-b]pyrazin-2(1H)-one;
7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-methoxyethyl)-3,4-dihydropyrazino[2,3-b]pyrazin-2(1H)-one;
7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;
7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;
7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;
7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;
7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;
7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(4-(1H-1,2,4-triazol-5-yl)phenyl)-1-(2-(tetrahydro-2H-pyran-4-yl)ethyl)-3,4-

TABLE A-continued dihydropyrazino[2,3-b]pyrazin-2(1H)-one;
1-(1-hydroxypropan-2-yl)-7-(2-methyl-6-(1H-1,2,4-triazol-3-yl)pyridin-3-yl)-3,4-
dihydropyrazino[2,3-b]pyrazin-2(1H)-one; and
1-(2-hydroxyethyl)-7-(2-methyl-6-(1H-1,2,4-triazol-3-yl)pyridin-3-yl)-3,4-dihydropyrazino[2,3-
b]pyrazin-2(1H)-one, and pharmaceutically acceptable salts, clathrates, solvates, stereoisomers, tautomers, metabolites, isotopologues and prodrugs thereof.

4.3 Methods for Making TOR Kinase Inhibitors

The TOR kinase inhibitors can be obtained via standard, well-known synthetic methodology, see e.g., March, J. Advanced Organic Chemistry; Reactions Mechanisms, and Structure, 4th ed., 1992. Starting materials useful for preparing compounds of formula (III) and intermediates therefore, are commercially available or can be prepared from commercially available materials using known synthetic methods and reagents.

Particular methods for preparing compounds of formula (I) are disclosed in U.S. Pat. No. 8,110,578, issued Feb. 7, 2012, and U.S. Pat. No. 8,569,494, issued Oct. 29, 2013, each incorporated by reference herein in their entirety.

4.4 Second Active Agents

Second active agents useful in combination with the TOR kinase inhibitors are provided below.

4.4.1 Receptor Tyrosine Kinase (RTK) Inhibitors

In some embodiments, the second active agent is a RTK inhibitor. In certain embodiments, the RTK inhibitor is PF-04217903, Cabozantinib (Cometrig™ or XL184), Crizotinib (Xalkori™), INCB28060 (INC280), GSK1904529A, BMS-754807, AST-1306, Erlotinib (Tarceva™), Lapatinib (Tykerb™/Tyverb™), Sunitinib (Sutent™ or SU11248) or Sorafenib (Nexavar™). In some embodiments, the receptor tyrosine kinase is EGFR. In some such embodiments, the second active agent is an EGFR inhibitor, for example, Erlotinib or Lapatinib.

4.4.2 Phosphoinositide 3-Kinase (PI3K) Pathway Inhibitors

In some embodiments, the second active agent is a PI3K inhibitor. In certain embodiments, the PI3K inhibitor is AT7867, AZD 8055, BX-912, CX-4945, GDC-0941, MK-2206, XL147 (SAR245408).

4.4.3 Serine/Threonine-Protein Kinase (RAF) and Mitogen-Activated Protein Kinase/Extracellular Signal-Regulated Protein Kinase Kinase (MEK) Pathway Inhibitors In some embodiments, the second active agent is a RAF/MEK pathway inhibitor. In certain embodiments, the RAF/MEK pathway inhibitor is AS703026, GDC-0879, PD0325901, ARRY142886, CI-1040, or Sorafenib (Nexavar™). In some such embodiments, the second active agent is a RAF inhibitor, for example, Sorafenib. In other embodiments, the second active is a MEK inhibitor, for example, ARRY142886 or CI-1040.

4.4.4 DNA Damaging Agents

In some embodiments, the second active agent is a DNA damaging agent. In certain embodiments, the DNA damaging agent is 10-HT, bleomycin (Blenoxane), capecitabine (Xeloda™), carboplatin (Paraplatin™ or Paraplatin-AQ™), cisplatin, dacarbazine (DTIC™, DTIC-Dome™; DIC or Imidazole Carboxamide), doxorubicin (Adriamycin™, Doxil™ or hydroxydaunorubicin), etoposide (VP-16 or Etopophos™), fluorouracil (5-FU, Adrucil (IV)™, Carac™ or Efudex™), gemcitabine (Gemzar™), irinotecan or melphalan (Sarcolysin or Alkeran™).

4.4.5 DNA Damage Response Agents

In some embodiments, the second active agent is a DNA damage response agent. In certain embodiments, the DNA damage response agent is ABT-888 (Veliparib), AZD7762, CGK733, JNJ 26854165 (Serdemetan), KU-60019, MK-1775, Nutlin-3, or AZD-228 (Olaparib). In some such embodiments, the DNA damage response agent is a PARP inhibitor, for example, AZD-228 (Olaparib), or ABT-888 (Veliparib).

4.4.6 Cytoskeleton Perturbagens

In some embodiments, the second active agent is a cytoskeleton perturbagen. In certain embodiments, the cytoskeleton perturbagen is AZD1152, BI 2536, Paclitaxel (Taxol®, Abraxane™ or Onxol™) or Vinblastine.

4.4.7 Protein Stability Inhibitors

In some embodiments, the second active agent is a protein stability inhibitor. In certain embodiments, the protein stability inhibitor is 17-DMAG, BIIB021 (CNF2024), Bortezomib (PS-341, Velcade™ or Cytomib™) or MLN-4924.

4.4.8 Bruton's Tyrosine Kinase (BTK) Inhibitors

In some embodiments, the second active agent is a BTK inhibitor. In certain embodiments, the BTK inhibitor is PCI-32765 (Ibrutinib or Imbruvica™).

4.4.9 Bcl-2 Protein Family Inhibitors

In some embodiments, the second active agent is a Bcl-2 protein family inhibitor. In some such embodiments, the Bcl-2 protein is selected from one or more of Bcl 2, Bcl-$X_L$, Mcl1, Bcl-W, A1 and Bcl-B. In some such embodiments, the Bcl-2 protein family inhibitor is a Bcl-2 inhibitor (for example, ABT-199, Obatoclax mesylate (GX15-070), or Oblimersen (Bcl-2 antisense)). In some other embodiments, the Bcl-2 protein family inhibitor is ABT-199. In another, the Bcl-2 protein family inhibitor is a Bcl-$X_L$ inhibitor (for example, WEHI-539). In yet another embodiment, the Bcl-2 protein family inhibitor is a Mcl1 inhibitor (for example, UMI-37, Maritoclax, or MIM-1). In still other embodiments, the Bcl-2 protein family inhibitor is a Bcl-2 and Bcl-$X_L$ inhibitor (for example, ABT-263 (Navitoclax), or ABT-737). In some such embodiments, the Bcl-2 and Bcl-$X_L$ inhibitor additionally inhibits Bcl-W (for example, ABT-263 (Navitoclax), or ABT-737). In another embodiment, the Bcl-2 protein family inhibitor is a Bcl-2, Mcl1, and Bcl-$X_L$ inhibitor (for example, TW-37, BH3 mimetic S1 [See Int J Cancer 2011; 128:1724-35], or BH3-M6). In yet another embodiment, the Bcl-2 protein family inhibitor is a Bcl-2, Bcl-$X_L$, Mcl1, and A1 inhibitor (for example, BI-97D6, or BIM-SAHB). In some other embodiments, the second active agent is a BAX activator (for example, BAM7). In some embodiments, the Bcl-2 protein family inhibitor is ABT-263 or ABT-737.

4.4.10 Second Active Agents

In certain embodiments, the second active agent is (+)-JQ1, 10-Hydroxycamptothecin, 17-DMAG, A769662, ABT-737, ABT-888 (Veliparib), ARRY142886, AS703026, AST-1306, AT7519, AT7867, AZD1152-HQPA (Barasertib), AZD7762, Bay 11-7082, BAY61-3606 Hydrochloride, Belinostat (PXD101), BI 2536, BIIB021 (CNF2024), Bleomycin Sulfate (Blenoxane), BMS-708163, BMS-754807, Bortezomib (PS-341, Velcade™ or Cytomib™), BX-912, Capecitabine (Xeloda™), Carboplatin (Paraplatin™ and Paraplatin-AQ™), CGK733, CHIR98014, CI-1040, Cisplatin, Crizotinib (Xalkori™), CX-4945, Dacarbazine (DTIC™, DTIC-Dome™; DIC or Imidazole Carboxamide), Doxorubicin HCl (Adriamycin™, Doxil™, hydroxydaunorubicin), Erlotinib Hydrochloride (Tarceva™), Etoposide (VP-16 or Etopophos™), FK-866, Fluorouracil (5-FU or Adrucil (IV)™, Carac™, Efudex™), Fulvestrant, GDC-0449, GDC-0879, GDC-0941, Gemcitabine Hydrochloride (Gemzar™), GF 109203X, GSK1904529A, GSK429286A, IMD-0354, INCB28060 (INC280), Irinotecan Hydrochloride, JNJ 26854165 (Serdemetan), KU-60019, Lapatinib (Tykerb™/Tyverb™), LY2228820, Melphalan (Sarcolysin or Alkeran™), Methotrexate, MK-2206, MLN-4924, MLN9708, MS-275 (Entinostat or SNDX-275), Nutlin-3, Oliparib, Paclitaxel (Taxol®, Abraxane™ or Onxol™), Parthenolide, PCI-32765 (Ibrutinib or Imbruvica™), PD0325901, PD-0332991, PF-04217903, Sorafenib (Nexavar™), SP 600125, Sunitinib Malate (Sutent™ or SU11248), Tamoxifen Citrate, UNC0646, Vinblastine Sulfate, XL147 (SAR245408), Cabozantinib (Cometrig™ or XL184), or YM155, as listed in the first column in Table 2a and Table 2b.

4.5 Methods of Use

The TOR kinase inhibitor and the second active agent provided herein can be used in all the methods provided herein. The TOR kinase inhibitor and the second active agent provided herein can be used in the treatment of all diseases, disorders or conditions provided herein.

Provided herein are methods for treating or preventing a cancer, comprising administering an effective amount of a TOR kinase inhibitor and an effective amount of a second active agent to a patient having a cancer.

In some embodiments, the methods provided herein comprise administering an effective amount of a TOR kinase inhibitor and an effective amount of a receptor tyrosine kinase inhibitor, a phosphoinositide 3-kinase pathway inhibitor, a serine/threonine-protein kinase and mitogen-activated protein kinase/extracellular signal-regulated protein kinase kinase pathway inhibitor, a DNA damaging agent, a DNA damage response agent, a cytoskeleton perturbagen, a protein stability inhibitor, a Bruton's tyrosine kinase inhibitor, or a Bcl-2 protein family inhibitor.

In certain embodiments, the cancer is a bloodborne tumor.

In certain embodiments, the cancer is a lymphoma, a leukemia or a multiple myeloma.

In certain embodiments, the cancer is non-Hodgkin's lymphoma. In certain embodiments, the non-Hodgkin's lymphoma is diffuse large B-cell lymphoma (DLBCL), follicular lymphoma (FL), acute myeloid leukemia (AML), mantle cell lymphoma (MCL), or ALK$^+$ anaplastic large cell lymphoma. In one embodiment, the non-Hodgkin's lymphoma is advanced solid non-Hodgkin's lymphoma. In one embodiment, the non-Hodgkin's lymphoma is diffuse large B-cell lymphoma (DLBCL).

In certain embodiments, the cancer is diffuse large B-cell lymphoma (DLBCL).

In certain embodiments, the cancer is a B-cell lymphoma.

In certain embodiments, the B-cell lymphoma is a B-cell non-Hodgkin's lymphoma selected from diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplasmacytic lymphoma/Waldenstrom macroglobulinemia. In some embodiments, the B-cell lymphoma is chronic lymphocytic leukemia/small lymphocytic lymphoma (CLL/SLL). In one embodiment, the B-cell lymphoma is Waldenstrom macroglobulinemia. In other embodiments, the CLL is characterized as the small lymphocytic lymphoma (SLL) variant of CLL.

In one embodiment, the B-cell non-Hodgkin's lymphoma is refractory B-cell non-Hodgkin's lymphoma. In one embodiment, the B-cell non-Hodgkin's lymphoma is relapsed B-cell non-Hodgkin's lymphoma.

In certain embodiments, the cancer is a T-cell lymphoma. In one embodiment, the T-cell lymphoma is peripheral T-cell lymphoma, or cutaneous T-cell lymphoma.

The B-cell disorders chronic lymphocytic leukemia/small lymphocytic lymphoma (CLL/SLL) represent 2 ends of a spectrum of the same disease process differing in the degree of blood/marrow involvement (CLL) versus lymph node involvement (SLL).

In other embodiments, the cancer is a multiple myeloma.

In certain embodiments, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments, the cancer is a solid tumor. In certain embodiments, the solid tumor is a relapsed or refractory solid tumor.

The solid tumor can be an advanced solid tumor.

The solid tumor can be a neuroendocrine tumor, glioblastoma multiforme (GBM), hepatocellular carcinoma (HCC), breast cancer, colorectal cancer (CRC), salivary cancer, pancreatic cancer, adenocystic cancer, adrenal cancer, esophageal cancer, renal cancer, leiomyosarcoma, paraganglioma, head and neck squamous cell carcinoma, E-twenty six (ETS) overexpressing castration-resistant prostate cancer or E-twenty six (ETS) overexpressing Ewings sarcoma.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the solid tumor is non-small cell lung cancer (NSCLC).

In another embodiment, the solid tumor is glioblastoma multiforme (GBM).

In another embodiment, the solid tumor is a carcinoma.

In another embodiment, the solid tumor is ductal carcinoma.

In another embodiment, the solid tumor is adenocarcinoma.

In another embodiment, the solid tumor is hepatocellular carcinoma (HCC).

In another embodiment, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment, the solid tumor is colorectal cancer (CRC).

In another embodiment, the solid tumor is salivary cancer.

In another embodiment, the solid tumor is pancreatic cancer.

In another embodiment, the solid tumor is adenocystic cancer.

In another embodiment, the solid tumor is adrenal cancer.

In another embodiment, the solid tumor is esophageal cancer, renal cancer, leiomyosarcoma, or paraganglioma.

In one embodiment, the solid tumor is an advanced solid tumor.

In another embodiment, the cancer is head and neck squamous cell carcinoma.

In another embodiment, the cancer is E-twenty six (ETS) overexpressing castration-resistant prostate cancer.

In another embodiment, the cancer is E-twenty six (ETS) overexpressing Ewings sarcoma.

In other embodiments, the cancer is a cancer associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

In certain embodiments, provided herein are methods for achieving an International Workshop on Chronic Lymphocytic Leukemia (IWCLL) response definition of a complete response, partial response or stable disease in a patient having chronic lymphocytic leukemia, comprising administering an effective amount of a TOR kinase inhibitor in combination with a second active agent to said patient. In certain embodiments, provided herein are methods for achieving a Response Evaluation Criteria in Solid Tumors (for example, RECIST 1.1) of complete response, partial response or stable disease in a patient having a solid tumor, comprising administering an effective amount of a TOR kinase inhibitor in combination with a second active agent to said patient. In certain embodiments, provided herein are methods for achieving a National Cancer Institute-Sponsored Working Group on Chronic Lymphocytic Leukemia (NCI-WG CLL) response definition of complete response, partial response or stable disease in a patient having leukemia, comprising administering an effective amount of a TOR kinase inhibitor in combination with a second active agent to said patient. In certain embodiments, provided herein are methods for achieving a Prostate Cancer Working Group 2 (PCWG2) Criteria of complete response, partial response or stable disease in a patient having prostate cancer, comprising administering an effective amount of a TOR kinase inhibitor in combination with a second active agent to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with a second active agent to said patient. In certain embodiments, provided herein are methods for achieving an International Uniform Response Criteria (IURC) for multiple myeloma of complete response, partial response or stable disease in a patient having multiple myeloma, comprising administering an effective amount of a TOR kinase inhibitor in combination with a second active agent to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering an effective amount of a TOR kinase inhibitor in combination with a second active agent to said patient.

In certain embodiments, provided herein are methods for increasing survival without disease progression of a patient having a cancer, comprising administering an effective amount of a TOR kinase inhibitor in combination with an effective amount of a second active agent to said patient.

In certain embodiments, provided herein are methods for treating a cancer, the methods comprising administering an effective amount of a TOR kinase inhibitor in combination with an effective amount of a second active agent to a patient having a cancer, wherein the treatment results in prevention or retarding of clinical progression, such as cancer-related cachexia or increased pain.

In some embodiments, provided herein are methods for treating a cancer, the methods comprising administering an effective amount of a TOR kinase inhibitor in combination with an effective amount of a second active agent to a patient having a B-cell lymphoma, wherein the treatment results in one or more of inhibition of disease progression, increased Time To Progression (TTP), increased Progression Free Survival (PFS), and/or increased Overall Survival (OS), among others.

In some embodiments, the TOR kinase inhibitor is a compound as described herein. In one embodiment, the TOR kinase inhibitor is a compound of formula (I). In one embodiment, the TOR kinase inhibitor is a compound from Table A. In one embodiment, the TOR kinase inhibitor is Compound 1 (a TOR kinase inhibitor set forth herein having molecular formula $C_{16}H_{16}N_8O$). In one embodiment, the TOR kinase inhibitor is Compound 2 (a TOR kinase inhibitor set forth herein having molecular formula $C_{21}H_{27}N_5O_3$). In one embodiment, the TOR kinase inhibitor is Compound 3 (a TOR kinase inhibitor set forth herein having molecular formula $C_{20}H_{25}N_5O_3$). In one embodiment, the TOR kinase inhibitor is Compound 4 (a TOR kinase inhibitor set forth herein having molecular formula $C_{21}H_{24}N_8O_2$). In another embodiment, Compound 1 is 1-ethyl-7-(2-methyl-6-(1H-1,2,4-triazol-3-yl)pyridin-3-yl)-3,4-dihydropyrazino[2,3-b]pyrazin-2(1H)-one, or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one. In one embodiment, Compound 2 is 7-(6-(2-hydroxypropan-2-yl)pyridin-3-yl)-

1-((1r,4r)-4-methoxycyclohexyl)-3,4-dihydropyrazino-[2,3-b]pyrazin-2(1H)-one, alternatively named 7-(6-(2-hydroxypropan-2-yl)pyridin-3-yl)-1-((trans)-4-methoxycyclohexyl)-3,4-dihydropyrazino[2,3-b]pyrazin-2(1H)-one, or 7-(6-(2-hydroxypropan-2-yl)pyridin-3-yl)-1-((1R*,4R*)-4-methoxycyclohexyl)-3,4-dihydropyrazino[2,3-b]pyrazin-2(1H)-one. In another embodiment, Compound 3 is 1-((trans)-4-hydroxycyclohexyl)-7-(6-(2-hydroxypropan-2-yl)pyridin-3-yl)-3,4-dihydropyrazino[2,3-b]pyrazin-2(1H)-one, alternatively named 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one. In another embodiment, Compound 4 is 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one. In one embodiment, Compound 3 is a metabolite of Compound 2.

A TOR kinase inhibitor administered in combination with a second active agent can be further combined with radiation therapy or surgery. In certain embodiments, a TOR kinase inhibitor is administered in combination with a second active agent to patient who is undergoing radiation therapy, has previously undergone radiation therapy or will be undergoing radiation therapy. In certain embodiments, a TOR kinase inhibitor is administered in combination with a second active agent to a patient who has undergone surgery, such as tumor removal surgery.

Further provided herein are methods for treating patients who have been previously treated for a cancer, as well as those who have not previously been treated. Because patients with a cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

In certain embodiments, a TOR kinase inhibitor is administered in combination with a second active agent to a patient in cycles. Cycling therapy involves the administration of an active agent(s) for a period of time, followed by a rest for a period of time, and repeating this sequential administration. Cycling therapy can reduce the development of resistance, avoid or reduce the side effects, and/or improves the efficacy of the treatment.

In some embodiments, a second active agent is administered twice daily, or BID, whereas a TOR kinase inhibitor is administered once daily, or QD. Alternatively and/or additionally, a second active agent may be administered once or twice daily for one or more 28-day cycles, whereas a TOR kinase inhibitor may be administered once daily for days 1 through 21 of one or more 28-day cycles. In some embodiments, a second active agent is administered twice daily on days 1 through 28 of one or more 28-day cycles and a TOR kinase inhibitor is administered once daily on days 2 through 22 of one or more 28-day cycles. In some embodiments, a second active agent is administered twice daily on days 1 through 28 of one or more 28-day cycles and a TOR kinase inhibitor is administered once daily on days 1 through 28 of one or more 28-day cycles.

In some embodiments, the provided methods comprise administering a second active agent in combination with a TOR kinase inhibitor daily for a period of 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, a treatment regimen comprises at least one 28-day cycle. As used herein, the term "28-day cycle" means that the combination of a second active agent and a TOR kinase inhibitor is administered to a patient in need thereof for 28 consecutive days. In some embodiments, the combination of a second active agent and a TOR kinase inhibitor is administered for at least one 28-day cycle. In some embodiments, the combination of a second active agent and a TOR kinase inhibitor is administered for at least two, at least three, at least four, at least five or at least six 28-day cycles. In some embodiments, the combination of a second active agent and a TOR kinase inhibitor is administered for at least seven, at least eight, at least nine, at least ten, at least eleven or at least twelve 28-day cycles. In some embodiments, the combination of a second active agent and a TOR kinase inhibitor is administered for at least thirteen, at least fourteen, at least fifteen, at least sixteen, at least seventeen or at least eighteen 28-day cycles.

In some embodiments, the combination of a second active agent and a TOR kinase inhibitor is administered for at least eighteen 28-day cycles, and a second active agent is further administered for at least one additional 28-day cycle. In some embodiments, the combination of a second active agent and a TOR kinase inhibitor is administered for at least eighteen 28-day cycles, and a second active agent is further administered for at least two, at least three, at least four, at least five, at least six, at least seven, at least eight, at least nine, at least ten, at least eleven or at least twelve additional 28-day cycles. In some embodiments, the combination of a second active agent and a TOR kinase inhibitor is administered for at least eighteen 28-day cycles, and a second active agent is further administered for at least thirteen, at least fourteen, at least fifteen, at least sixteen, at least seventeen, at least eighteen, at least nineteen, at least twenty, at least twenty-one, at least twenty-two, at least twenty-three or at least twenty-four additional 28-day cycles. In some embodiments, the combination of a second active agent and a TOR kinase inhibitor is administered to a patient for the duration of the patient's life. In some embodiments, the combination of a second active agent and a TOR kinase inhibitor is administered for at least eighteen 28-day cycles, and a second active agent is further administered for the duration of the patient's life. In some embodiments, a second active agent is administered on days 1 through 28 (for example, one dose each day or two doses each day) of each 28-day cycle and a second active agent is administered on days 1 through 21 (for example, one dose each day) of one or more 28-day cycles. In some embodiments, a second active agent is administered on days 1 through 28 of one or more 28-day cycles and a second active agent is administered on days 2 through 22 of one or more 28-day cycles.

In some embodiments, two adjacent 28-day cycles may be separated by a rest period. Such a rest period may be one, two, three, four, five, six, seven or more days during which the patient is not administered either or both a second active agent and a TOR kinase inhibitor. In a preferred embodiment, two adjacent 28-day cycles are continuous.

In one embodiment, a TOR kinase inhibitor is administered in combination with a second active agent daily in single or divided doses for about 3 days, about 5 days, about one week, about two weeks, about three weeks, about four weeks (e.g., 28 days), about five weeks, about six weeks, about seven weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, a TOR kinase inhibitor is administered in combination with a second active agent in single or divided doses for about 3 days, about 5 days, about one week, about two weeks, about three weeks, about four weeks (e.g., 28 days), about five weeks, or about six weeks with a rest period of about 1, 2, 3, 4, 5, 6, 7, 8, 9, 10, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, the methods provided herein comprise: i) administering to the subject a first daily dose of a TOR kinase inhibitor in combination with a second active agent; ii) optionally resting for a period of at least one day where a second active agent is not administered to the subject; iii) administering a second dose of a TOR kinase inhibitor in combination with a second active agent to the subject; and iv) repeating steps ii) to iii) a plurality of times.

In one embodiment, the methods provided herein comprise administering to the subject a dose of a second active agent on day 1, followed by administering a TOR kinase inhibitor in combination with a second active agent to the subject on day 2 and subsequent days.

In certain embodiments, a TOR kinase inhibitor in combination with a second active agent is administered continuously for between about 1 and about 52 weeks. In certain embodiments, a TOR kinase inhibitor in combination with a second active agent is administered continuously for about 0.5, 1, 2, 3, 4, 5, 6, 7, 8, 9, 10, 11, or 12 months. In certain embodiments, a TOR kinase inhibitor in combination with a second active agent is administered continuously for about 7, about 14, about 21, about 28, about 35, about 42, about 84, or about 112 days.

In certain embodiments, when a TOR kinase inhibitor is administered in combination with a second active agent, the TOR kinase inhibitor is administered continuously for 28 days, while a second active agent is administered continuously for 21 days followed by 7 days without administration of a second active agent. In one embodiment, in a 28 day cycle, a second active agent is administered alone on Day 1, a second active agent and the TOR kinase inhibitor are administered in combination on Days 2-21 and the TOR kinase inhibitor is administered alone on Days 22-28. In some such embodiments, starting with Cycle 2 both a second active agent and the TOR kinase inhibitor are administered on Day 1, a second active agent is continued through Day 21, while the TOR kinase inhibitor is continued through Day 28. The 28 day cycles, as described above, can be continued for as long needed, such as for 1, 2, 3, 4, 5, 6, 7, 8, 9, 10, 11 or 12 months or longer.

In certain embodiments, when a TOR kinase inhibitor is administered in combination with a second active agent, in a 28 day cycle, a second active agent is administered alone on Days 1-7 and the TOR kinase inhibitor is administered alone on Days 8-28. Such 28 day cycles can be continued for as long needed, such as for 1, 2, 3, 4, 5, 6, 7, 8, 9, 10, 11 or 12 months or longer.

In certain embodiments, when a TOR kinase inhibitor is administered in combination with a second active agent, the TOR kinase inhibitor is administered at an amount of about 2.5 mg to about 50 mg per day (such as about 2.5 mg, about 10 mg, about 15 mg, about 16 mg/day, about 20 mg, about 30 mg or about 45 mg per day) and a second active agent is administered at an amount of about 125 mg to about 1250 mg per day (such as about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day). In certain embodiments, about 2.5 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. In certain embodiments, about 10 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. In certain embodiments, about 15 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. In certain embodiments, about 16 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. In certain embodiments, about 20 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. In certain embodiments, about 30 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. In certain embodiments, about 45 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of a second active agent. A TOR kinase inhibitor and a second active agent can each be independently administered once (QD), twice (BD) or three times (TID) per day.

In some embodiments, methods provided herein comprise administering to a patient in need thereof a therapeutically effective amount of a TOR kinase inhibitor in combination with a second active agent, wherein the therapeutically effective amount of a second active agent is about 250 mg to about 1250 mg per day. In some embodiments, the therapeutically effective amount of a second active agent is administered as one or more discreet doses. For example, in some embodiments, a therapeutically effective amount of a second active agent is 250 mg per day, wherein the therapeutically effective amount is administered as 125 mg twice daily (BID). In some embodiments, a therapeutically effective amount of a second active agent is 500 mg per day, wherein the therapeutically effective amount is administered as 250 mg twice daily (BID). In some embodiments, a therapeutically effective amount of a second active agent is 750 mg per day, wherein the therapeutically effective amount is administered as 375 mg twice daily (BID). In some embodiments, a therapeutically effective amount of a second active agent is 1000 mg per day, wherein the therapeutically effective amount is administered as 500 mg twice daily (BID).

In some embodiments, methods provided herein comprise administering to a patient in need thereof a therapeutically effective amount of a TOR kinase inhibitor in combination with a second active agent, wherein the therapeutically effective amount of a second active agent is about 125 mg to about 1250 mg per day, or about 125 mg to about 1125 mg per day, or about 125 mg to about 1000 mg per day, or about 125 mg to about 875 mg per day, or about 125 mg to about 750 mg per day, or about 125 mg to about 625 mg per day, or about 125 mg to about 500 mg per day, or about 125 mg to about 375 mg per day, or about 125 mg to about 250 mg per day, or about 250 mg to about 1250 mg per day, or about 250 mg to about 1125 mg per day, or about 250 mg to about 1000 mg per day, or about 250 mg to about 875 mg per day, or about 250 mg to about 750 mg per day, or about 250 mg to about 625 mg per day, or about 250 mg to about 500 mg per day, or about 250 mg to about 375 mg per day, or about 375 mg to about 1250 mg per day, or about 375 mg to about 1125 mg per day, or about 375 mg to about 1000 mg per day, or about 375 mg to about 875 mg per day, or about 375 mg to about 750 mg per day, or about 375 mg to about 625 mg per day, or about 375 mg to about 500 mg per day, or about 500 mg to about 1250 mg per day, or about 500 mg to about 1125 mg per day, or about 500 mg to about 1000 mg per day, or about 500 mg to about 875 mg per day, or about 500 mg to about 750 mg per day, or about 500 mg to about 625 mg per day, or about 625 mg to about 1250 mg per day, or about 625 mg to about 1125 mg per day, or about 625 mg to about 1000 mg per day, or about 625 mg to about 875 mg per day, or about 625 mg to about 750 mg per day, or about 750 mg to about 1250 mg per day, or about 750 mg to about 1125 mg per day, or about 750 mg to about 1000 mg per day, or about 875 mg to about 1250 mg per day, or about 875 mg to about 1125 mg per day, or about 875 mg to about 1000 mg per day.

In some embodiments, methods provided herein comprise administering to a patient in need thereof a therapeutically effective amount of a TOR kinase inhibitor in combination with a second active agent, wherein the therapeutically effective amount of a second active agent per day is about 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1000 mg, 1005 mg, 1010 mg, 1015 mg, 1020 mg, 1025 mg, 1030 mg, 1035 mg, 1040 mg, 1045 mg, 1050 mg, 1055 mg, 1060 mg, 1065 mg, 1070 mg, 1075 mg, 1080 mg, 1085 mg, 1090 mg, 1095 mg, 1100 mg, 1105 mg, 1110 mg, 1115 mg, 1120 mg, 1125 mg, 1130 mg, 1135 mg, 1140 mg, 1145 mg, 1150 mg, 1155 mg, 1160 mg, 1165 mg, 1170 mg, 1175 mg, 1180 mg, 1185 mg, 1190 mg, 1195 mg, 1200 mg, 1205 mg, 1210 mg, 1215 mg, 1220 mg, 1225 mg, 1230 mg, 1235 mg, 1240 mg, 1245 mg or 1250 mg.

In some embodiments, the methods of treatment provided herein comprise administering to a patient in need thereof about 125 mg BID to about 500 mg BID a second active agent in combination with about 2.5 mg to about 50 mg per day (such as about 2.5 mg, about 10 mg, about 15 mg, about 16 mg/day, about 20 mg, about 30 mg or about 45 mg per day) of a TOR kinase inhibitor. In some embodiments, provided methods comprise administering to a patient in need thereof 375 mg BID to about 500 mg BID a second active agent in combination with about 2.5 mg to about 50 mg (such as about 2.5 mg, about 10 mg, about 15 mg, about 16 mg/day, about 20 mg, about 30 mg or about 45 mg per day) of a TOR kinase inhibitor.

4.6 Pharmaceutical Compositions and Routes of Administration

Provided herein are compositions comprising an effective amount of a TOR kinase inhibitor and an effective amount of a second active agent and compositions comprising an effective amount of a TOR kinase inhibitor and a second active agent and a pharmaceutically acceptable carrier or vehicle.

In some embodiments, the pharmaceutical compositions described herein are suitable for oral, parenteral, mucosal, transdermal or topical administration.

The compositions can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the TOR kinase inhibitor in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a TOR kinase inhibitor and the dose of a second active agent to be administered to a patient is rather widely variable and can be subject to the judgment of a health-care practitioner. In general, the TOR kinase inhibitors and a second active agent can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the TOR kinase inhibitor administered will depend on such factors as the solubility of the active component, the formulation used and the route of administration.

In another embodiment, provided herein are unit dosage formulations that comprise between about 1 mg and about 2000 mg, about 1 mg and about 200 mg, about 35 mg and about 1400 mg, about 125 mg and about 1000 mg, about 250 mg and about 1000 mg, about 500 mg and about 1000 mg, about 1 mg to about 30 mg, about 1 mg to about 25 mg or about 2.5 mg to about 20 mg of a TOR kinase inhibitor alone or in combination with a second active agent. In another embodiment, provided herein are unit dosage formulations that comprise 1 mg, 2.5 mg, 5 mg, 7.5 mg, 8 mg, 10 mg, 15 mg, 20 mg, 30 mg, 35 mg, 45 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a TOR kinase inhibitor alone or in combination with a second active agent. In another embodiment, provided herein are unit dosage formulations that comprise about 2.5 mg, about 7.5 mg, about 8 mg, about 10 mg, about 15 mg, about 20 mg, about 30 mg or about 45 mg of a TOR kinase inhibitor alone or in combination with a second active agent.

In a particular embodiment, provided herein are unit dosage formulations comprising about 7.5 mg, about 8 mg, about 10 mg, about 15 mg, about 30 mg, about 45 mg, about 50 mg, about 75 mg, about 100 mg or about 400 mg of a TOR kinase inhibitor in combination with a second active agent. In a particular embodiment, provided herein are unit dosage formulations comprising about 5 mg, about 7.5 mg or about 10 mg of a TOR kinase inhibitor in combination with a second active agent.

In certain embodiments, provided herein are unit dosage formulations comprising about 25 mg, about 50 mg, about 75 mg, about 100 mg, about 125 mg, about 150 mg, about 175 mg, about 200 mg, about 225 mg or about 250 mg of a second active agent alone or in combination with a TOR kinase inhibitor.

A TOR kinase inhibitor can be administered in combination with a second active agent once, twice, three, four or more times daily.

A TOR kinase inhibitor can be administered in combination with a second active agent orally for reasons of convenience. In one embodiment, when administered orally, a TOR kinase inhibitor in combination with a second active agent is administered with a meal and water. In another embodiment, the TOR kinase inhibitor in combination with a second active agent is dispersed in water or juice (e.g., apple juice or orange juice) and administered orally as a suspension. In another embodiment, when administered orally, a TOR kinase inhibitor in combination with a second active agent is administered in a fasted state.

The TOR kinase inhibitor can also be administered in combination with a second active agent intravenously, such as intravenous infusion, or subcutaneously, such as subcutaneous injection. The mode of administration is left to the discretion of the health-care practitioner, and can depend in-part upon the site of the medical condition.

In one embodiment, provided herein are capsules containing a TOR kinase inhibitor in combination with a second active agent without an additional carrier, excipient or vehicle.

In another embodiment, provided herein are compositions comprising an effective amount of a TOR kinase inhibitor, an effective amount of a second active agent, and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a TOR kinase inhibitor with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with filmforming protecting agents to modify the dissolution properties of the tablet. The compositions can also be formulated as chewable tablets, for example, by using substances such as mannitol in the formulation.

When it is desired to administer a TOR kinase inhibitor in combination with a second active agent as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the TOR kinase inhibitor in combination with a second active agent can be delayed or prolonged by proper formulation. For example, a slowly soluble pellet of the TOR kinase inhibitor in combination with a second active agent can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the TOR kinase inhibitor in combination with a second active agent in oily or emulsified vehicles that allow it to disperse slowly in the serum.

In some embodiments, a pharmaceutically acceptable composition comprising a second active agent comprises from about 5% to about 60% of a second active agent, or a pharmaceutically acceptable salt thereof, based upon total weight of the composition. In some embodiments, a pharmaceutically acceptable composition comprising a second active agent comprises from about 5% to about 15% or about 7% to about 15% or about 7% to about 10% or about 9% to about 12% of a second active agent, based upon total weight of the composition. In some embodiments, provided methods comprise administering to a patient in need thereof a pharmaceutically acceptable composition comprising from about 25% to about 75% or about 30% to about 60% or about 40% to about 50% or about 40% to about 45% of a second active agent, based upon total weight of the formulation. In certain embodiments, provided regimens comprise administering to a patient in need thereof a pharmaceutically acceptable composition comprising from about 6%, about 7%, about 8%, about 9%, about 10%, about 11%, about 12%, about 13%, about 20%, about 30%, about 40%, about 41%, about 42%, about 43%, about 44%, about 45%, about 50%, about 60%, about 70%, or about 75% of a second active agent, based upon total weight of given composition or formulation.

In certain embodiments, the Compound 2 is administered in a formulation set forth in U.S. Patent Application Publication No. 2013-0142873, published Jun. 6, 2013, which is incorporated herein in its entirety (see particularly paragraph [0323] to paragraph [0424], and paragraph [0636] to paragraph [0655]). In other embodiments, the Compound 2 is administered in a formulation set forth in U.S. Provisional Patent Application No. 61/828,506, filed May 29, 2013, which is incorporated herein in its entirety (see particularly paragraph [0246] to paragraph [0403], and paragraph [0571] to paragraph [0586]).

In certain embodiments, the Compound 1 is administered in a formulation set forth in U.S. Provisional Application No. 61/813,064, filed Apr. 17, 2013, which is incorporated herein in its entirety (see particularly paragraph [0168] to paragraph [0189] and paragraph [0262] to paragraph [0294]). In other embodiments, the Compound 1 is administered in a formulation set forth in U.S. Provisional Patent Application No. 61/911,201, filed Dec. 3, 2013, which is incorporated herein in its entirety (see particularly paragraph [0170] to paragraph [0190], and paragraph [0264] to paragraph [0296]).

4.7 Kits

In certain embodiments, provided herein are kits comprising a TOR kinase inhibitor and a second active agent, such as those described herein.

In certain embodiments, provided herein are kits comprising one or more unit dosage forms of a TOR kinase inhibitor, such as those described herein, and one or more unit dosage forms of a second active agent, such as those described herein.

In certain embodiments, the kits provided herein further comprise instructions for use, such as for administering a TOR kinase inhibitor and a second active agent, such as those described herein.

5. EXAMPLES

5.1 Cell Based Assays

Compound 1 Combinatorial Effects with Second Active Agents in Breast Cancer Cell Lines.

Anti-Proliferation Assay.

Cells were thawed from a liquid nitrogen preserved state. Once cells expanded and divided at their expected doubling times, screening began. Cells were seeded in growth media in 384-well tissue culture treated plates at cell densities as listed in Table 1.

TABLE 1

Breast cancer cell line panel

| Cell Line Name | Tumor | Growth Media | Cell Density (cells/well) |
| --- | --- | --- | --- |
| BT-20 | Carcinoma | Eagles MEM with 10% FBS | 500 |
| BT-474 | Carcinoma | Hybri-Care with 10% FBS | 500 |
| BT-549 | Carcinoma, Ductal | RPMI with 10% FBS and 0.023 IU/ml Bovine Insulin | 500 |
| HCC1187 | Carcinoma, Ductal | RPMI with 10% FBS | 500 |
| HCC-1428 | Adenocarcinoma | RPMI with 10% FBS | 500 |
| HCC1806 | Carcinoma, Ductal | RPMI with 10% FBS | 500 |
| HCC1937 | Carcinoma, Ductal | RPMI with 10% FBS | 500 |
| HCC70 | Carcinoma, Ductal | RPMI with 10% FBS | 500 |

TABLE 1-continued

Breast cancer cell line panel

| Cell Line Name | Tumor | Growth Media | Cell Density (cells/well) |
|---|---|---|---|
| Hs-578-T | Carcinoma | DMEM with 10% FBS and 0.01 mg/ml Bovine Insulin | 500 |
| MCF7 | Adenocarcinoma | Eagles MEM with 10% FBS and 0.01 mg/ml Bovine Insulin | 500 |
| MDA-MB-157 | Carcinoma | RPMI with 10% FBS (with 5% $CO_2$) | 500 |
| MDA-MB-231 | Adenocarcinoma | RPMI with 10% FBS (with 5% $CO_2$) | 500 |
| MDA-MB-436 | Adenocarcinoma | RPMI with 10% FBS (with 5% $CO_2$) plus Supplements | 500 |
| MDA-MB-453 | Adenocarcinoma | RPMI with 10% FBS (with 5% $CO_2$) | 500 |
| MDA-MB-468 | Adenocarcinoma | DMEM with 10% FBS (with 5% $CO_2$) | 500 |
| HCC1500 | Carcinoma, Ductal | RPMI with 10% FBS | 500 |
| MDA-MB-175-VII | Carcinoma, Ductal | RPMI with 10% FBS | 500 |

Cells were equilibrated in assay plates via centrifugation and placed in incubators attached to the Dosing Modules at 37° C. for twenty-four hours before treatment. At the time of treatment, a set of assay plates (which did not receive treatment) were collected and ATP levels were measured by adding ATP Lite (Perkin Elmer). These T zero ($T_0$) plates were read using ultra-sensitive luminescence on Envision Plate Readers. Treated assay plates were incubated with compound (single compound or combination) for seventy-two hours. After seventy-two hours, platesweare developed for endpoint analysis using ATPLite. All data points were collected via automated processes; quality controlled; and analyzed. Assay plates were accepted if they passed the following quality control standards: relative luciferase values were consistent throughout the entire experiment, Z-factor scoresweare greater than 0.6, untreated/vehicle controls behaved consistently on the plate. The calculation for synergy score is provided below.

Growth Inhibition (GI) was used as a measure of cell viability. The cell viability of vehicle was measured at the time of dosing ($T_0$) and after seventy-two hours ($T_{72}$). A GI reading of 0% represents no growth inhibition—cells treated with compound and $T_{72}$ vehicle signals are matched. A GI 100% represents complete growth inhibition—cells treated by compound and $T_0$ vehicle signals are matched. Cell numbers have not increased during the treatment period in wells with GI 100% and may suggest a cytostatic effect for compounds reaching a plateau at this effect level. A GI 200% represents complete death of all cells in the culture well. Compounds reaching an activity plateau of GI 200% are considered cytotoxic. GI is calculated by applying the following test and equation:

If $T<V_0$: $100*[1-(T-V_0)/V_0]$

If $T≥V_0$: $100*[1-(T-V_0)/(V-V_0)]$ where T is the signal measure for a test article, V is the vehicle-treated control measure, and $V_0$ is the vehicle control measure at time zero. This formula is derived from the Growth Inhibition calculation used in the National Cancer Institute's NCI-60 high throughput screen.

Synergy Score Analysis.

Synergy scores were determined using the Chalice Software (Zalicus Inc., Cambridge Mass.). Briefly, to measure combination effects in excess of Loewe additivity, a scalar measure to characterize the strength of synergistic interaction termed the Synergy Score was used. The Synergy Score is calculated as:

$$\text{Synergy Score} = \log f_X \log F_Y \Sigma_{max}(0, I_{data})(I_{data} - I_{Loewe})$$

wherein $I_{data}$ is the observed inhibition at a given combination of drug concentrations.

The calculation for additivity is:

$I_{Loewe}$ that satisfies $(X/X_I)+(Y/Y_I)=1$, where $X_I$ and $Y_I$ are the single agent effective concentrations for the observed combination effect I.

Activity observed in excess of Loewe additivity identifies potential synergistic interaction.

The fractional inhibition for each component agent and combination point in the matrix was calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) were used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels.

Self-Cross-Based Combination Screen Analysis.

Combinations where the synergy score is greater than the mean self-cross plus two standard deviations (2&s) can be considered candidate synergies at the 95% confidence level.

In order to objectively establish hit criteria for the combination screen analysis, twenty compounds were selected to be self-crossed across the seventeen cell line panel as a means to empirically determine a baseline additive, non-synergistic response. The identity of the twenty self-cross compounds was determined by selecting compounds with a variety of maximum response values and single agent dose response steepness. Those drug combinations which yielded effect levels that statistically superseded those baseline additivity values were considered synergistic.

Compound 1 had varying activity across the seventeen cell line panel. For each cell line, a three-fold, ten-point dose titration was performed in 384-well plate format. For cell lines where the $GI_{50}$ reached inhibition levels of greater than fifty percent, the median $GI_{50}$ was 0.14 µM. Synergy scores for treatment of breast cancer cell line panel with Compound 1 and second active agents are provided in Table 2a and Table 2b. Synergy scores that exceed the mean self-cross thresholds plus two standard deviations (2a) are depicted in bold.

Conclusion:

As can be seen in Table 2a and Table 2b, Compound 1 in combination with certain second active agents showed synergistic effects in multiple breast cancer cell lines.

TABLE 2a

Effects of Compound 1 in combination with second active agents on cell line colony formation of certain breast cancer cell lines. Synergy scores that exceed the mean self-cross thresholds plus two standard deviations (2σ) are depicted in bold. Each data point represents the mean of n = 3 experiments in triplicate.

| | BT-20 | BT-474 | BT-549 | HCC-1187 | HCC-1428 | HCC-1500 | HCC-1806 | HCC-1937 |
|---|---|---|---|---|---|---|---|---|
| (+)-JQ1 | 6.42 | 12.00 | 18.90 | 9.89 | 10.20 | 5.15 | 20.40 | 23.60 |
| 10-Hydroxy-camptothecin | 6.15 | 1.20 | 4.11 | 6.49 | 4.13 | 4.43 | 3.88 | 12.40 |
| 17-DMAG | 5.94 | 2.24 | 0.01 | 0.33 | 2.46 | 0.99 | 1.40 | 1.70 |
| A769662 | 0.11 | | 0.29 | 3.70 | 0.34 | 0.80 | 0.54 | 0.07 |
| ABT-737 | 7.28 | 4.14 | 6.10 | 8.77 | 10.60 | 4.23 | 6.15 | 5.46 |
| ABT-888 | 0.33 | 0.09 | 0.35 | 1.28 | 0.09 | 1.13 | 0.56 | 0.35 |
| AS703026 | 6.08 | 2.61 | 1.73 | 8.22 | 6.26 | 4.24 | 4.71 | 2.41 |
| AST-1306 | 7.60 | 4.02 | 4.88 | 2.17 | 2.69 | 0.96 | 5.59 | 6.39 |
| AT7519 | 4.95 | 0.19 | 4.33 | 1.57 | 1.58 | 0.03 | 1.01 | 2.04 |
| AT7867 | 3.07 | 1.83 | 4.50 | 4.19 | 1.42 | 2.00 | 2.04 | 1.72 |
| AZD8055 | 0.70 | 1.53 | 0.98 | 2.00 | 1.79 | 2.98 | 1.47 | 2.24 |
| AZD1152-HQPA (Barasertib) | 6.90 | 1.51 | 2.21 | 6.69 | 1.95 | 5.73 | 1.32 | 2.29 |
| AZD7762 | 3.92 | 1.21 | 0.39 | 1.65 | 2.58 | 3.02 | 0.32 | 4.44 |
| Bay 11-7082 | 0.00 | 0.93 | 1.16 | 0.51 | 1.53 | 0.52 | 1.01 | 1.23 |
| BAY61-3606 Hydrochloride | 0.20 | 0.04 | 2.31 | 3.17 | 1.21 | 0.02 | 0.48 | 0.18 |
| BI 2536 | 5.18 | 9.25 | 6.91 | 3.28 | 2.64 | 4.47 | 0.43 | 16.20 |
| BIIB021 | 3.71 | 2.83 | 0.12 | 0.45 | 4.02 | 1.11 | 1.01 | 1.44 |
| Bleomycin Sulfate | 1.46 | 0.65 | 0.52 | 2.20 | 1.27 | 1.91 | 0.62 | 2.73 |
| BMS-708163 | 0.20 | 0.19 | 0.34 | 3.06 | 0.26 | 0.34 | 0.89 | 0.96 |
| BMS-754807 | 2.08 | 1.30 | 2.14 | 9.68 | 4.09 | 3.99 | 3.04 | 0.64 |
| Bortezomib | 2.93 | 0.58 | 2.66 | 3.01 | 1.46 | 1.37 | 5.67 | 4.75 |
| BX-912 | 1.32 | 0.87 | 1.52 | 4.10 | 2.05 | 2.11 | 0.57 | 0.44 |
| Capecitabine | 0.25 | 0.77 | 0.17 | 1.53 | 0.65 | 1.82 | 0.51 | 1.52 |
| Carboplatin | 0.98 | 0.30 | 0.72 | 2.20 | 0.52 | 1.46 | 0.44 | 2.46 |
| CGK733 | 0.72 | 1.57 | 1.74 | 2.01 | 0.82 | 0.55 | 1.51 | 1.48 |
| CHIR98014 | 0.17 | 0.02 | 0.49 | 3.13 | 0.72 | | 1.56 | 0.63 |
| Crizotinib | 2.70 | 1.07 | 0.94 | 2.32 | 1.59 | 1.76 | 3.08 | 2.90 |
| CX-4945 | 6.09 | 4.91 | 3.41 | 7.53 | 3.28 | 2.93 | 4.19 | 7.92 |
| Dacarbazine | | 0.71 | 0.25 | 2.89 | 0.06 | 1.21 | 0.99 | 0.89 |
| Doxorubicin Hcl | 3.96 | 1.25 | 4.78 | 4.45 | 0.96 | 2.70 | 3.55 | 6.92 |
| Erlotinib Hydrochloride | 9.18 | 4.28 | 1.78 | 7.44 | 2.34 | 1.62 | 3.00 | 4.10 |
| Etoposide | 2.65 | 0.45 | 1.57 | 2.89 | 0.23 | 2.55 | 0.60 | 3.44 |
| FK-866 | 0.30 | 0.60 | 0.11 | 0.25 | 0.20 | 1.15 | 0.00 | 0.60 |
| Fluorouracil | 0.00 | 0.79 | 0.71 | 1.91 | 0.34 | 0.32 | 0.85 | 0.63 |
| Fulvestrant | 1.39 | 1.37 | 1.25 | 2.16 | 1.09 | 5.15 | 1.30 | 1.98 |
| GDC-0449 | 0.11 | 1.47 | 0.19 | 3.07 | 0.07 | 0.78 | 0.20 | 0.88 |
| GDC-0879 | 0.00 | 0.46 | 0.08 | 0.85 | 0.13 | 0.91 | 0.47 | 0.29 |
| GDC-0941 | 6.56 | 5.04 | 4.39 | 5.18 | 1.90 | 1.45 | 6.16 | 4.39 |
| Gemcitabine Hydrochloride | 1.85 | 0.17 | 1.86 | 1.83 | | | 3.72 | 0.84 | 3.78 |
| GF 109203X | 1.04 | 0.47 | 1.73 | 4.47 | 0.47 | 3.41 | 0.43 | 3.03 |
| GSK1904529A | 1.07 | 1.09 | 0.81 | 1.68 | 0.16 | 1.63 | 1.00 | 1.86 |
| GSK429286A | | | 1.72 | 4.54 | | 0.19 | 0.51 | 0.05 |
| IMD-0354 | 1.85 | 1.77 | 2.68 | 1.86 | 0.51 | 1.42 | 7.45 | 6.42 |
| INCB28060 | | 2.35 | 0.66 | 2.94 | 0.75 | 0.52 | 0.62 | 0.71 |
| Irinotecan Hydrochloride | 2.59 | 1.17 | 1.25 | 3.01 | 0.76 | 4.45 | 2.21 | 3.92 |
| JNJ 26854165 | 1.42 | 1.77 | 0.78 | 1.63 | 1.02 | 1.50 | 2.51 | 2.82 |
| KU-60019 | 0.05 | | 0.18 | 1.24 | 0.11 | 0.98 | 0.38 | 0.04 |
| Lapatinib | 5.30 | 2.33 | 0.98 | 2.35 | 0.91 | 1.12 | 5.01 | 3.59 |
| LY2228820 | 0.20 | 2.81 | 1.26 | 0.80 | 1.80 | 3.91 | 2.81 | 2.55 |
| Melphalan | 0.16 | 0.64 | 0.69 | 3.43 | 0.19 | 1.99 | 0.24 | 1.13 |
| Methotrexate | 0.01 | 0.62 | 0.73 | 1.94 | 0.27 | 1.92 | 0.59 | 0.69 |
| MK1775 | 5.01 | 9.61 | 2.99 | 1.30 | 3.25 | 2.46 | 0.55 | 7.93 |
| MK-2206 | 13.10 | 8.24 | 9.17 | 10.60 | 4.09 | 2.02 | 7.33 | 11.40 |
| MLN-4924 | 1.78 | 8.59 | 2.83 | 7.09 | 3.68 | 1.31 | 2.90 | 9.15 |
| MLN9708 | 3.67 | 0.75 | 4.47 | 1.79 | 2.59 | 2.26 | 4.31 | 3.84 |
| Nutlin-3 | 0.27 | 0.34 | 0.40 | 2.08 | 0.33 | 2.54 | 0.79 | 0.58 |
| Paclitaxel | 3.29 | 1.86 | 6.61 | 2.21 | 2.95 | 2.44 | 0.33 | 4.30 |

TABLE 2a-continued

Effects of Compound 1 in combination with second active agents on cell line colony formation of certain breast cancer cell lines. Synergy scores that exceed the mean self-cross thresholds plus two standard deviations (2σ) are depicted in bold. Each data point represents the mean of n = 3 experiments in triplicate.

|  | BT-20 | BT-474 | BT-549 | HCC-1187 | HCC-1428 | HCC-1500 | HCC-1806 | HCC-1937 |
|---|---|---|---|---|---|---|---|---|
| Parthenolide | 1.58 | 3.44 | 3.73 | 2.08 | 6.17 | 1.04 | 1.89 | 0.93 |
| PCI-32765 | 6.26 | 5.95 | 0.05 | 1.70 | 0.59 | 0.56 | 3.72 | 1.62 |
| PD0325901 | 6.34 | 1.50 | 1.62 | 7.89 | 4.69 | 3.58 | 3.78 | 3.54 |
| PD-0332991 | 2.65 | 0.31 | 1.10 | 2.76 | 2.01 | 2.71 | 1.54 | 0.55 |
| PF-04217903 | 0.05 | 0.57 | 0.04 | 0.17 | 0.31 | 0.11 | 0.39 | 0.44 |
| Sorafenib | 1.16 | 2.32 | 0.00 | 0.64 | 0.17 | 0.69 | 0.18 | 2.10 |
| SP 600125 | 0.00 | 0.72 | 1.47 | 5.59 | 1.44 | 1.15 | 1.16 | 0.87 |
| Sunitinib Malate |  | 0.47 | 0.36 | 2.95 | 0.36 | 0.20 | 0.82 | 0.28 |
| Tamoxifen Citrate | 1.12 | 1.07 | 0.82 | 2.11 | 0.09 | 1.58 | 2.54 | 2.12 |
| UNC 0646 | 2.59 | 1.13 | 0.91 | 0.22 | 1.66 | 1.11 | 0.53 | 0.54 |
| Vinblastine Sulfate | 3.47 | 2.83 | 6.91 | 1.69 | 2.63 | 2.15 | 0.89 | 6.27 |
| XL147 | 0.23 | 1.81 | 0.18 | 5.02 | 0.43 | 2.87 | 1.06 | 0.64 |
| XL184 | 3.67 | 1.51 | 0.52 | 1.29 | 1.19 | 1.20 | 1.44 | 2.15 |
| YM155 | 2.67 | 4.04 | 6.80 | 4.94 | 1.16 | 2.81 | 5.52 | 5.70 |
| Mean + 2σs | 3.23 | 3.37 | 3.94 | 4.80 | 3.22 | 4.17 | 5.05 | 2.89 |

***p < 0.001 vs theoretical additivity by unpaired t test.

TABLE 2b

Effects of Compound 1 in combination with second active agents on cell line colony formation of certain breast cancer cell lines. Synergy scores that exceed the mean self-cross thresholds plus two standard deviations (2σ) are depicted in bold. Each data point represents the mean of n = 3 experiments in triplicate. ***p < 0.001 vs theoretical additivity by unpaired t test.

|  | HCC-70 | Hs-578-T | MCF7 | MDA-MB-157 | MDA-MB-175-VII | MDA-MB-231 | MDA-MB-436 | MDA-MB-453 | MDA-MB-468 |
|---|---|---|---|---|---|---|---|---|---|
| (+)-JQ1 | 19.60 | 18.50 | 9.41 | 16.20 | 8.77 | 10.30 | 7.83 | 21.30 | 30.00 |
| 10-Hydroxycamptothecin | 6.31 | 1.70 | 3.80 | 10.30 | 3.84 | 8.55 | 3.62 | 7.55 | 7.86 |
| 17-DMAG | 11.10 | 0.45 | 0.13 | 6.09 | 7.09 | 1.00 | 0.61 | 24.70 | 7.72 |
| A769662 | 0.07 | 0.39 | 0.46 | 0.70 | 1.05 | 0.17 | 0.06 | 0.37 | 0.77 |
| ABT-737 | 9.10 | 10.00 | 6.97 | 4.46 | 8.33 | 10.00 | 0.56 | 10.60 | 8.29 |
| ABT-888 | 1.10 | 0.42 | 0.25 | 0.90 | 0.87 | 0.22 | 0.32 | 0.67 | 0.18 |
| AS703026 | 13.70 | 6.43 | 2.90 | 6.66 | 13.20 | 10.90 | 2.25 | 1.79 | 5.71 |
| AST-1306 | 7.50 | 4.43 | 4.34 | 3.02 | 5.27 | 4.37 | 2.08 | 12.00 | 5.65 |
| AT7519 | 0.86 | 5.16 | 2.84 | 5.37 | 1.87 | 2.68 | 2.57 | 3.63 | 1.98 |
| AT7867 | 4.28 | 5.24 | 1.39 | 3.19 | 3.56 | 3.58 | 1.95 | 4.44 | 3.60 |
| AZD8055 | 1.13 | 1.55 | 1.22 | 1.04 | 1.02 | 0.61 | 0.15 | 1.05 | 1.69 |
| AZD1152-HQPA(Barasertib) | 9.50 | 2.43 | 2.57 | 1.81 | 4.49 | 1.42 | 5.60 | 1.20 | 9.13 |
| AZD7762 | 4.61 | 8.16 | 0.08 | 3.09 | 5.09 | 3.66 | 0.93 | 0.02 | 0.94 |
| Bay 11-7082 | 1.13 | 1.51 | 0.02 | 3.65 | 1.48 | 0.61 | 1.24 | 2.34 | 1.89 |
| BAY61-3606 Hydrochloride | 3.93 | 5.49 | 1.49 | 1.49 | 0.62 | 0.79 | 0.94 | 0.10 | 5.47 |
| Belinostat | 10.10 | 7.48 | 7.66 | 7.58 | 3.21 | 12.40 | 7.84 | 14.80 | 6.75 |
| BI 2536 | 12.60 | 4.48 | 3.30 | 5.08 | 2.32 | 2.92 | 2.95 | 2.02 | 9.61 |
| BIIB021 | 9.58 | 1.19 | 0.15 | 3.94 | 7.40 | 1.22 | 0.33 | 15.50 | 5.46 |
| Bleomycin Sulfate | 1.43 | 2.70 | 1.08 | 6.00 | 2.21 | 2.34 | 3.57 | 0.25 | 4.70 |
| BMS-708163 | 1.24 | 1.36 | 0.16 | 0.63 | 0.76 | 1.45 | 0.86 | 0.11 | 0.98 |
| BMS-754807 | 2.08 | 3.32 | 5.31 | 9.46 | 2.31 | 2.50 | 2.00 | 1.17 | 2.25 |
| Bortezomib | 3.65 | 2.20 | 1.77 | 3.81 | 3.03 | 1.28 | 3.90 | 1.41 | 4.83 |
| BX-912 | 6.05 | 6.07 | 0.69 | 6.65 | 1.48 | 2.21 | 2.50 | 3.91 | 8.29 |
| Capecitabine | 0.73 | 1.19 | 0.47 | 1.04 | 0.40 | 0.46 | 0.12 | 0.48 | 0.37 |
| Carboplatin | 2.26 | 1.65 | 0.80 | 1.77 | 1.84 | 0.45 | 1.10 | 0.88 | 7.18 |
| CGK733 | 3.03 | 2.45 | 0.66 | 1.88 | 1.94 | 1.64 | 0.84 | 0.58 | 2.82 |
| CHIR98014 | 0.82 | 5.48 | 0.29 | 3.17 | 0.48 | 3.91 | 0.04 | 0.04 | 3.00 |
| Crizotinib | 3.31 | 3.19 | 3.06 | 2.97 | 1.43 | 1.59 | 1.30 | 0.13 | 1.41 |
| CX-4945 | 10.60 | 5.97 | 2.26 | 4.55 | 3.55 | 2.30 | 1.70 | 1.52 | 6.73 |
| Dacarbazine | 0.73 | 0.88 | 0.12 | 2.49 | 0.05 | 0.09 | 0.34 | 0.66 | 0.23 |
| Doxorubicin Hcl | 4.00 | 5.85 | 2.65 | 8.50 | 6.83 | 6.45 | 3.89 | 7.40 | 6.36 |
| Erlotinib Hydrochloride | 7.53 | 2.11 | 2.35 | 2.36 | 6.17 | 0.92 | 1.26 | 0.88 | 6.38 |
| Etoposide | 5.13 | 4.17 | 3.29 | 5.33 | 2.82 | 1.14 | 2.52 | 2.64 | 7.19 |
| FK-866 | 0.30 | 5.32 | 0.04 | 1.43 | 1.27 |  | 0.97 | 0.23 | 0.28 |
| Fluorouracil | 2.57 | 1.50 | 0.29 | 1.30 | 0.26 | 0.35 | 0.33 | 0.32 | 0.60 |

TABLE 2b-continued

Effects of Compound 1 in combination with second active agents on cell line colony formation of certain breast cancer cell lines. Synergy scores that exceed the mean self-cross thresholds plus two standard deviations (2σ) are depicted in bold. Each data point represents the mean of n = 3 experiments in triplicate. ***$p < 0.001$ vs theoretical additivity by unpaired t test.

|  | HCC-70 | Hs-578-T | MCF7 | MDA-MB-157 | MDA-MB-175-VII | MDA-MB-231 | MDA-MB-436 | MDA-MB-453 | MDA-MB-468 |
|---|---|---|---|---|---|---|---|---|---|
| Fulvestrant | 1.50 | 2.10 | 2.45 | 0.42 | 0.42 | 0.77 | 0.74 | 0.67 | 0.41 |
| GDC-0449 | 1.10 | 0.28 | 0.21 | 0.77 | 0.04 | 0.08 | 0.19 | 0.21 | 0.44 |
| GDC-0879 | 0.43 | 0.75 | 0.11 | 0.69 | 0.43 | 0.54 | 0.13 | 0.52 | 0.44 |
| GDC-0941 | 6.42 | 7.23 | 5.22 | 5.60 | 6.24 | 1.76 | 1.25 | 12.10 | 3.21 |
| Gemcitabine Hydrochloride | 2.55 | 0.96 | 0.38 | 2.53 | 1.12 | 2.51 | 3.05 | 0.48 | 5.52 |
| GF 109203X | 4.47 | 2.35 | 0.35 | 6.19 | 4.08 | 2.28 | 2.60 | 2.24 | 10.60 |
| GSK1904529A | 2.15 | 0.97 | 2.77 | 0.82 | 2.85 | 0.09 | 1.22 | 0.53 | 2.44 |
| GSK429286A | 1.57 | 3.35 | 0.19 | 1.95 | 0.16 | 2.14 | 0.57 | 1.25 | 0.13 |
| IMD-0354 | 0.88 | 3.35 | 2.88 | 4.80 | 3.37 | 6.14 | 3.94 | 1.91 | 3.80 |
| INCB28060 | 0.75 | 0.85 | 0.92 | 0.97 | 1.32 | 0.34 | 0.49 | 0.44 | 0.80 |
| Irinotecan Hydrochloride | 1.98 | 2.73 | 2.02 | 5.71 | 2.75 | 1.64 | 3.61 | 2.85 | 8.45 |
| JNJ 26854165 | 2.46 | 1.28 | 1.82 | 2.53 | 2.54 | 0.31 | 1.47 | 0.47 | 3.28 |
| KU-60019 | 0.21 | 0.11 | 0.04 | 0.13 | 0.22 | 0.08 | 0.21 | 0.49 | 0.19 |
| Lapatinib | 8.14 | 3.37 | 4.59 | 1.54 | 4.11 | 0.28 | 0.92 | 5.76 | 3.85 |
| LY2228820 | 3.65 | 2.89 | 3.76 | 5.64 | 4.90 | 2.18 | 1.32 | 0.48 | 5.77 |
| Melphalan | 1.34 | 1.83 | 0.24 | 2.83 | 2.03 | 0.54 | 1.61 | 1.12 | 5.31 |
| Methotrexate | 1.76 | 1.77 | 0.57 | 1.68 | 0.22 | 0.05 | 0.22 | 0.96 | 1.53 |
| MK1775 | 12.10 | 9.02 | 5.76 | 2.68 | 4.58 | 2.31 | 1.45 | 1.08 | 7.69 |
| MK-2206 | 13.30 | 12.60 | 12.10 | 9.00 | 11.90 | 3.39 | 5.55 | 27.90 | 10.80 |
| MLN-4924 | 0.46 | 3.55 | 0.94 | 6.73 | 4.38 | 2.34 | 1.43 | 0.63 | 15.10 |
| MLN9708 | 2.16 | 1.68 | 0.39 | 2.91 | 3.69 | 2.27 | 2.77 | 0.60 | 3.00 |
| MS-275 | 9.37 | 8.44 | 7.69 | 8.10 | 6.71 | 11.70 | 7.83 | 14.60 | 9.25 |
| Nutlin-3 | 2.72 | 1.65 | 2.05 | 0.66 | 2.44 | 0.27 | 0.50 | 0.23 | 1.08 |
| Paclitaxel | 6.92 | 5.69 | 5.01 | 3.38 | 3.18 | 4.26 | 3.18 | 1.78 | 8.92 |
| Parthenolide | 3.02 | 5.40 | 0.06 | 2.47 | 1.87 | 0.10 | 1.95 | 5.69 | 7.80 |
| PCI-32765 | 6.29 | 1.04 | 0.13 | 3.28 | 6.86 | 0.27 | 0.07 | 8.31 | 3.10 |
| PD0325901 | 14.70 | 3.88 | 4.62 | 8.05 | 11.60 | 9.62 | 4.20 | 1.79 | 5.84 |
| PD-0332991 | 2.17 | 0.75 | 2.48 | 0.73 | 2.69 | 2.88 | 0.44 | 1.04 | 2.12 |
| PF-04217903 | 0.33 | 1.12 | 0.20 | 0.75 | 0.22 | 0.53 | 0.08 |  | 1.09 |
| Romidepsin | 6.74 | 9.01 | 6.17 | 5.71 | 6.30 | 9.27 | 5.84 | 13.80 | 7.26 |
| Sorafenib | 2.51 | 1.65 | 1.18 | 0.56 | 2.25 | 1.55 | 1.35 | 0.17 | 0.63 |
| SP 600125 | 3.49 | 0.97 | 0.75 | 1.18 | 4.51 | 0.65 | 0.79 | 0.81 | 2.55 |
| Sunitinib Malate | 2.39 | 0.83 | 0.60 | 1.30 | 1.76 | 0.09 | 0.92 | 0.82 | 1.16 |
| Tamoxifen Citrate | 2.22 | 2.73 | 1.96 | 2.48 | 2.99 | 0.29 | 0.72 | 1.09 | 1.20 |
| UNC0646 | 2.03 | 2.20 | 3.27 | 1.05 | 0.03 | 0.49 | 0.66 | 0.09 | 2.08 |
| Vinblastine Sulfate | 6.93 | 5.26 | 6.32 | 5.19 | 2.51 | 2.58 | 3.37 | 1.83 | 7.24 |
| XL147 | 0.09 | 0.77 | 0.18 | 1.99 | 0.70 | 0.57 | 0.67 | 0.54 | 0.34 |
| XL184 | 1.47 | 3.19 | 4.34 | 5.13 | 2.20 | 1.08 | 0.90 | 0.32 | 1.84 |
| YM155 | 4.01 | 3.36 | 1.77 | 5.42 | 1.97 | 2.54 | 2.79 | 1.36 | 0.24 |
| Mean + 2σs | 3.45 | 4.09 | 3.07 | 4.68 | 2.82 | 2.61 | 1.91 | 2.99 | 4.66 |

5.2 Compound 1 and Compound 2 Combinatorial Effects with +JQ1 in Cancer Cell Lines Anti-Proliferation Assay.

Cells were grown, treated and analyzed as described above, and synergy was calculated using the Chalice Software (Zalicus, Inc., Cambridge Mass.), described above.

Cell lines used included T47D (human ductal breast epithelial tumor cell line), MCF (adenocarcinoma breast cancer cell line), MDA-MM468 (adenocarcinoma breast cancer cell line), HCC-70 (carcinoma, ductal breast cancer cell line), SKBR-3 (adenocarcinoma breast cancer cell line), MM-453 (adenocarcinoma breast cancer cell line).

TABLE 3

+JQ1 combination treatment with Compound 1 and Compound 2.

| | Chalice Calculated Synergy Scores | | | | | | | | Averages | |
|---|---|---|---|---|---|---|---|---|---|---|
| Cell line | Compound 1 & +JQ1 | | | | Compound 2 & +JQ1 | | | | Compound 1 | Compound 2 |
| T47-D | 8.45 | 12.09 | 9.22 | 5.18 | 3.30 | 6.96 | 2.72 | 3.11 | 8.74 | 4.02 |
| MCF-7 | 10.16 | 7.03 | 5.90 | 6.38 | 2.06 | 1.79 | 2.05 | 2.38 | 7.37 | 2.07 |
| MM-468 | 23.38 | 13.69 | 20.90 | 11.07 | 12.78 | 9.33 | 10.85 | 13.35 | 17.26 | 11.58 |
| HCC-70 | 11.66 | 16.22 | 8.27 | | 6.22 | 3.94 | 7.78 | | 12.05 | 5.98 |
| SKBR-3 | 8.39 | 11.41 | 8.73 | 9.82 | 5.95 | 7.57 | 5.44 | 5.61 | 9.59 | 6.14 |
| MM-453 | 15.20 | 16.87 | 17.03 | | 3.93 | 6.99 | 10.17 | | 16.37 | 7.03 |

Conclusion: Synergism was observed for the treatment with +JQ1 and Compound 1 or Compound 2.

5.3 Compound 1 and Compound 2 Combinatorial Effects with Additional Second Agents Materials and Methods.

Cell lines and cell culture: Cell lines were purchased from American Type Culture Collection (ATCC) and maintained in culture medium recommended by ATCC. Non-small cell lung cancer (NSCLC) cell lines that were used or can be used include the following: NCI-H460, NCI-H838, NCI-H1792, NCI-H520, NCI-H1993, NCI-H1944, NCI-H1975, NCI-H1395, A549, NCI-H2122, NCI-H1703, NCI-H1299, NCI-H647, NCI-H358, SK-LU-1, NCI-H1734, NCI-H1693, NCI-H226, NCI-H23, NCI-H2030, NCI-H1755, Calu-6, Calu-1, SW1573, NCI-H2009, NCI-H441, HOP92, NCI-H2110, NCI-H727, NCI-H1568, Calu-3, NCI-H2228, NCI-H2444, NCI-H1563, NCI-H1650, NCI-H1437, NCI-H650, NCI-H1838, NCI-H2291, NCI-H28 and NCI-H596. Ovarian cancer cell lines that were used or can be used include the following: Ovcar-3, Ovcar-4, Ovcar-5, Oncar-8 and Caov-3. Hepatocellular cancer, breast cancer, lung cancer and melanoma cell lines were purchased from commercial sources (ATCC, DSMZ, HSRRB) and routinely maintained in RPMI1640 or DMEM containing 10% fetal bovine serum at 37° C. with 5% $CO_2$. Hepatocellular carcinoma (HCC) cell lines that were used or can be used include the following: Hep3B, HepG2, HuH-7, PLC-PRF-5, SK-HEP-1, SNU-182, SNU-387, SNU-398, SNU-423, SNU-449, and SNU-387. Breast cell lines that were used or can be used include the following: BT-20, BT-549, CAL-120, CAL-51, CAL-85-1, DU4475, HCC1187, HCC1954, HS578T, MCF-7, MDA-MB-157, MDA-MB-231, MDA-MB-436, MDA-MB-468, and SK-BR-3. Melanoma cell lines that were used or can be used include the following: Malme-3M or UACC-257.

Cell Viability Assay for NSCLC and Ovarian Cell Lines.

Cell viability was assessed using the Cell Titer-Glo® Luminescent Cell Viability Assay, Catalog Number G7570 (Promega Corporation, Madison, Wis.). The assay is a homogenous method of determining the number of viable cells in culture based on quantitation of the adenosine triphosphate (ATP) present, an indicator of metabolically active cells. The homogenous assay procedure involves adding the single reagent (CellTiter-Glo Reagent) directly to cells cultured in serum-supplemented medium. Cells were plated into a 96-well flat bottom plate (Costar Catalog Number 33595) at densities that were previously optimized for each cell line. The cells were incubated overnight in 5% $CO_2$ at 37° C. The following day, compound dilutions were prepared and all concentrations were assayed in triplicate. The cells were incubated with TOR kinase inhibitor, or TOR kinase inhibitor and second active agent, in 5% $CO_2$ at 37° C. for 3 days. After a 3-day incubation period, 100 µL of CellTiter-Glo reagent was added to each well for 2 min with shaking and further incubated for 10 min (no shaking) at room temperature to stabilize the signal. The luminescence was measured on the VICTOR X2 multilabel plate reader. The percent growth inhibition was calculated using the DMSO control in the same plate (no compound) response as 100% cell growth. For single compound treatments (TOR kinase inhibitor and second active agents separately), the average values from triplicates were plotted to obtain $IC_{50}$ values using software XLfit from IDBS. The formula used for determining $IC_{50}$ in XLfit was model number 205, which utilizes a 4 Parameter Logistic Model or Sigmoidal Dose-Response Model to calculate the $IC_{50}$ values. Results are set forth in Table 4, Table 5, Table 6 and Table 7.

Measurement of Synergism of Cell Proliferation Inhibition Using TOR Kinase Inhibitor in Combination with Second Active Agent.

The cell viability assay was first performed with the TOR kinase inhibitor and the individual second active agents, to determine the dose range for subsequent combination studies. To maintain similar potency for the TOR kinase inhibitor and the second active agent, the highest combination dose started at the approximate $IC_{50}$ for each compound, with a constant ratio of 1:1 or 1:10 during dilutions. The TOR kinase inhibitor and the second active agent were each added to one well containing a final concentration of 0.2% DMSO (in triplicate). In the same plate in triplicate, the cells were treated with the TOR kinase inhibitor and each second active agent either simultaneously or sequentially (containing 0.2% DMSO). The number of cells affected by compound treatment was normalized to the DMSO control (100% viability) and the data was imported into the CalcuSyn software (V2.1, Biosoft). Synergism was quantitated by the combination index (CI) using CalcuSyn according to Chou-Talalay's CI method with mathematical modeling and simulations. The CI value indicates strong synergism if the value is between 0.1-0.3, synergism between 0.3-0.7, moderate synergism 0.7-0.85, slight synergism 0.85-0.90 and nearly additive 0.90-1.10 (*Trends Pharmacol. Sci.* 4, 450-454, 1983). $ED_{50}$ is the median effect dose at which a 50% growth inhibition is achieved. Results are set forth in Table 4, Table 5, Table 6 and Table 7.

TABLE 4

Combination index (CI) in selected NSCLC cell lines for Compound 2 and a MEK inhibitor (MEKi) ARRY142886.

| NSCLC | Compound 2 + ARRY142886 CI at ED50 |
|---|---|
| A549 | 0.235 |
| H460 | 0.229 |
| H1734 | 0.421 |
| H2030 | 0.416 |
| Calu-6 | 0.016 |
| Calu-1 | 0.016 |
| HOP62 | 0.676 |
| H23 | 0.398 |
| H647 | 0.635 |
| H441 | 0.004 |
| H1703 | 0.766 |
| H1993 | 0.319 |
| H226 | 0.129 |
| HOP92 | 0.379 |
| H520 | 0.990 |
| H522 | 0.119 |
| H1299 | 0.280 |
| H1650 | 0.002 |

TABLE 5

Combination index (CI) in selected NSCLC cell lines for Compound 2 and an EGFR inhibitor (EGFRi), Erlotinib

| NSCLC (KRAS) | Combination | CI at ED50 |
|---|---|---|
| A549 | Compound 2 + Erlotinib | 0.374 |
| H460 | Compound 2 + Erlotinib | 0.422 |
| H647 | Compound 2 + Erlotinib | 0.465 |
| H2030 | Compound 2 + Erlotinib | 0.353 |

TABLE 6

Combination index (CI) in ovarian cancer cell lines for Compound 2 and Cisplatin

| | Compound 2 | |
|---|---|---|
| Cell line | Simultaneous treatment CI at $ED_{50}$ | 24 hour pre-treatment with Cisplatin CI at $ED_{50}$ |
| Ovcar-3 | 0.87 | 2.04 |
| Ovcar-5 | 0.42 | 0.31 |
| Ovcar-8 | 0.97 | 0.84 |
| SK-OV-3 | 0.95 | 0.49 |

TABLE 7

Combination index (CI) in ovarian cancer cell lines for Compound 2 and Taxol

| | Compound 2 | |
|---|---|---|
| Cell line | Simultaneous treatment CI at ED50 | 24 h pre-treatment with Paclitaxel CI at ED50 |
| Ovcar-3 | 0.87 | 0.22 |
| Ovcar-5 | 1.13 | 0.38 |
| Ovcar-8 | 0.71 | 0.5 |

Cell Viability Assay for Hepatocellular, Breast, Lung, and Melanoma Cell Lines.

The TOR kinase inhibitor and second agent were added to an empty 384-well flat, clear bottom, black polystyrene, TC-Treated plate (Cat#3712, Corning, Mass.) via an acoustic dispenser (EDC Biosystems). The TOR kinase inhibitor was serially diluted 3-fold across the plate for nine concentrations and the second agent was serially diluted 3-fold down the plate for seven concentrations. An orthogonal titration of the two agents was performed to create 63 different combinations of the compounds. Both compounds were also added alone to determine their affects as single agents. DMSO (no compound) was used as control for 100% viability and background (no cells). Final assay DMSO concentration was 0.2% (v/v). Cells were added directly on top of the compounds at an optimized density to ensure that the cell growth was within the linear detection range of the assay after four days in culture. At its endpoint, cell viability was determined using Promega's CellTiter-Glo Luminescent Cell Viability Assay (Cat#G7573, Promega, WI) using the manufacturer's standard operating procedures. Background subtracted luminescence counts were converted to percentages of cell viability with respect to DMSO treated control cells. Dose response curves were generated using XLFit4 (IDBS, UK) by fitting the percentage of control data at each concentration using a 4 Parameter Logistic Model/Sigmoidal Dose-Response Model [y=(A+4B−A)/(1+((C/x)^D)))]. To evaluate the combinatorial effect of the two agents on a cell line, data was analyzed by comparing its combinatorial response against the theoretical additive response of the two agents alone. The expected additive effect of two agents (A and B) was calculated using the fractional product method (Webb 1961): (fu)A,B=(fu)A×(fu)B where fu=fraction unaffected by treatment. Synergism of a combination is determined when the observed fraction unaffected in combination is less than (fu)A,B, while an additive effect is determined when the observed fraction unaffected in combination=(fu)A,B. Results are set forth in Table 8, Table 9 and Table 10.

TABLE 8

Combination of Compound 2 and second active agents in selected HCC cell lines

| HCC cell line | Combination | Synergism |
|---|---|---|
| Hep3B | Compound 2 + Erlotinib | Synergy |
| | Compound 2 + Sorafenib | Weak Synergy |
| | Compound 2 + ARRY142886 | Additive |
| HepG2 | Compound 2 + Erlotinib | Strong Synergy |
| | Compound 2 + Sorafenib | Additive |
| | Compound 2 + ARRY142886 | Additive |
| HuH-7 | Compound 2 + ARRY142886 | Weak Synergy |
| | Compound 2 + Erlotinib | Synergy |
| | Compound 2 + Sorafenib | Weak Synergy |
| PLC-PRF-5 | Compound 2 + ARRY142886 | Additive |
| | Compound 2 + Erlotinib | Synergy |
| | Compound 2 + Sorafenib | Weak Synergy |
| SK-HEP-1 | Compound 2 + Sorafenib | Additive |
| SNU-182 | Compound 2 + ARRY142886 | Synergy |
| | Compound 2 + Erlotinib | Weak Synergy |
| | Compound 2 + Sorafenib | Synergy |
| SNU-387 | Compound 2 + Erlotinib | Weak Synergy |
| | Compound 2 + Sorafenib | Weak Synergy |
| | Compound 2 + ARRY142886 | Additive |
| SNU-398 | Compound 2 + ARRY142886 | Synergy |
| | Compound 2 + Sorafenib | Additive |
| SNU-423 | Compound 2 + ARRY142886 | Weak Synergy |
| | Compound 2 + Erlotinib | Synergy |
| | Compound 2 + Sorafenib | Weak Synergy |
| SNU-449 | Compound 2 + Erlotinib | Additive |
| | Compound 2 + Sorafenib | Additive |
| SNU-475 | Compound 2 + Erlotinib | Synergy |
| | Compound 2 + Sorafenib | Weak Synergy |
| | Compound 2 + ARRY142886 | Synergy |

TABLE 9

Combination of Compoudn 1 and Compound 2 and second active agents in selected breast cancer cell lines

| Breast Cell Line | Combination | Synergism |
|---|---|---|
| BT-20 | Compound 2 + Erlotinib | Synergy |
| BT-20 | Compound 1 + Erlotinib | Synergy |
| BT-549 | Compound 2 + Erlotinib | Additive |
| BT-549 | Compound 2 + Olaparib | Weak Synergy |
| BT-549 | Compound 1 + Erlotinib | Synergy |
| BT-549 | Compound 1 + Olaparib | Additive |
| CAL-120 | Compound 2 + Erlotinib | Weak Synergy |
| CAL-120 | Compound 1 + Erlotinib | Weak Synergy |
| CAL-120 | Compound 1 + Olaparib | Additive |
| CAL-148 | Compound 2 + Olaparib | Strong Synergy |
| CAL-148 | Compound 1 + Olaparib | Additive |
| CAL-51 | Compound 2 + Erlotinib | Synergy |
| CAL-51 | Compound 2 + Olaparib | Additive |
| CAL-51 | Compound 1 + Erlotinib | Synergy |
| CAL-51 | Compound 1 + Olaparib | Additive |
| CAL-85-1 | Compound 2 + Erlotinib | Weak Synergy |
| CAL-85-1 | Compound 2 + Olaparib | Additive |
| CAL-85-1 | Compound 1 + Erlotinib | Synergy |
| CAL-85-1 | Compound 1 + Olaparib | Additive |
| DU4475 | Compound 2 + Olaparib | Additive |
| DU4475 | Compound 1 + Olaparib | Synergy |
| HCC1143 | Compound 2 + Erlotinib | Synergy |
| HCC1143 | Compound 1 + Erlotinib | Weak Synergy |
| HCC1187 | Compound 2 + Erlotinib | Synergy |
| HCC1187 | Compound 1 + Erlotinib | Strong Synergy |
| HCC1187 | Compound 1 + Olaparib | Additive |
| HCC1806 | Compound 2 + Erlotinib | Weak Synergy |
| HCC1806 | Compound 1 + Erlotinib | Weak Synergy |
| HCC1937 | Compound 2 + Erlotinib | Additive |
| HCC1937 | Compound 1 + Erlotinib | Weak Synergy |
| HCC1954 | Compound 2 + Lapatinib | Synergy |
| HCC2157 | Compound 2 + Erlotinib | Additive |
| HCC2157 | Compound 2 + Olaparib | Additive |
| HCC2157 | Compound 1 + Erlotinib | Additive |

TABLE 9-continued

Combination of Compoudn 1 and Compound 2 and second active agents in selected breast cancer cell lines

| Breast Cell Line | Combination | Synergism |
|---|---|---|
| HCC2157 | Compound 1 + Olaparib | Additive |
| HCC38 | Compound 2 + Olaparib | Additive |
| HCC38 | Compound 1 + Olaparib | Additive |
| HCC70 | Compound 2 + Erlotinib | Synergy |
| HCC70 | Compound 1 + Erlotinib | Weak Synergy |
| HDQ-P1 | Compound 2 + Erlotinib | Synergy |
| HDQ-P1 | Compound 1 + Erlotinib | Synergy |
| HS578T | Compound 2 + Erlotinib | Weak Synergy |
| HS578T | Compound 2 + Olaparib | Additive |
| HS578T | Compound 1 + Erlotinib | Synergy |
| HS578T | Compound 1 + Olaparib | Weak Synergy |
| MB157 | Compound 2 + Erlotinib | Additive |
| MB157 | Compound 1 + Olaparib | Additive |
| MDA-MB-157 | Compound 2 + Olaparib | Weak Synergy |
| MDA-MB-231 | Compound 2 + Erlotinib | Weak Synergy |
| MDA-MB-231 | Compound 2 + Olaparib | Additive |
| MDA-MB-231 | Compound 1 + Erlotinib | Additive |
| MDA-MB-231 | Compound 1 + Olaparib | Additive |
| MDA-MB-436 | Compound 2 + Erlotinib | Additive |
| MDA-MB-468 | Compound 2 + Erlotinib | Weak Synergy |
| MDA-MB-468 | Compound 2 + Olaparib | Additive |
| MDA-MB-468 | Compound 1 + Erlotinib | Synergy |
| MT-3 | Compound 2 + Erlotinib | Weak Synergy |
| MT-3 | Compound 2 + Olaparib | Weak Synergy |
| MT-3 | Compound 1 + Erlotinib | Weak Synergy |
| MT-3 | Compound 1 + Olaparib | Additive |
| SK-BR-3 | Compound 2 + Lapatinib | Additive |

TABLE 10

Combination of Compound 1 and Compound 2 and second active agents in selected NSCLC cell line

| Lung cell line | Combination | Synergism |
|---|---|---|
| A549 | Compound 2 + Erlotinib | Weak Synergy |
|  | Compound 1 + Erlotinib | Additive |
|  | Compound 2 + Olaparib | Weak Synergy |
|  | Compound 1 + Olaparib | Additive |

Caspase-Glo 3/7 Assay for Tor Kinase Inhibitor in Combination with Second Active Agent.

Cell lines were maintained in the growth medium recommended by ATCC (American Type Culture Collection). The induction of caspase 3/7 by the TOR kinase inhibitor alone and by the TOR kinase inhibitor and the second active agent was assessed by Caspase Glo® 3/7 Luminescent Assay, Catalog Number G8091 (Promega Corporation, Madison, Wis.) after 24 hour treatment. The compounds were serially diluted in DMSO from the highest concentration of 30 μM (single compounds and in combination with constant a constant ratio of 1:1). The TOR kinase inhibitor or the TOR kinase inhibitor and the second active agent were used in each well at a final concentration of 0.2% DMSO (in triplicate). The percentage of induction of apoptosis was normalized to DMSO control (no compound).

TABLE 11

Combination of Compound 2 and a MEKi CI-1040 results in increased caspase 3/7 activation in NCI-H441 cells at 24 hours post-treatment (data is normalized to DMSO control in the same plate)

| Concentration | Compound 2 (% Caspase activation) Mean (n = 3) | SD | CI-1040 (% Caspase activation) Mean (n = 3) | SD | Compound 2 + CI-1040 at 1:1 (% Caspase activation) Mean (n = 3) | SD |
|---|---|---|---|---|---|---|
| 30 μM | 85.5 | 8.3 | 124.2 | 9.2 | 167 | 1.5 |
| 10 μM | 80 | 5 | 103.9 | 3.5 | 171.9 | 18.2 |
| 3 μM | 77.7 | 15 | 99.3 | 3.3 | 129.9 | 19.6 |
| 1 μM | 67.7 | 3.6 | 96.6 | 2.6 | 107.5 | 22 |
| 0.3 μM | 66.4 | 4.6 | 104.1 | 13.9 | 93.1 | 4 |
| 0.1 μM | 69.9 | 10.9 | 98.6 | 7.9 | 95.9 | 9.7 |

A number of references have been cited, the disclosures of which are incorporated herein by reference in their entirety. The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

What is claimed is:

1. A method for inhibiting target of rapamycin activity in a patient, comprising administering to the patient an effective amount of 1-ethyl-7-(2-methyl-6-(4H-1,2,4-triazol-3-yl)pyridin-3-yl)-3,4-dihydropyrazino[2,3-b]pyrazin-2(1H)-one, or a pharmaceutically acceptable salt, stereoisomer or tautomer thereof, in combination with an effective amount of a second active agent, wherein the second active agent is selected from the group consisting of a receptor tyrosine kinase inhibitor, a phosphoinositide 3-kinase pathway inhibitor, a serine/threonine-protein kinase and mitogen-activated protein kinase/extracellular signal-regulated protein kinase kinase pathway inhibitor, a deoxyribonucleic acid damaging agent, a deoxyribonucleic acid damage response agent, a cytoskeleton perturbagen, a protein stability inhibitor, a Bruton's tyrosine kinase inhibitor and a B-cell lymphoma-2 protein family inhibitor, wherein:

the receptor tyrosine kinase inhibitor is selected from the group consisting of

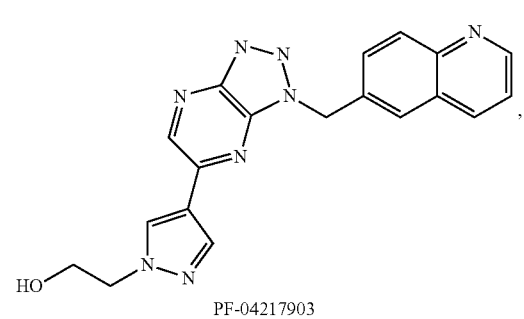

PF-04217903

-continued
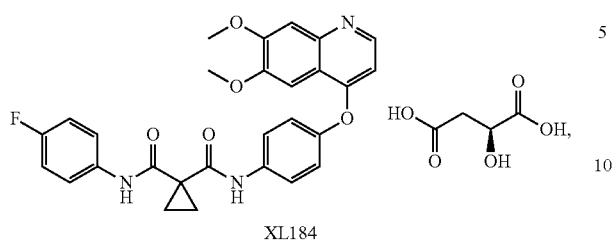
XL184
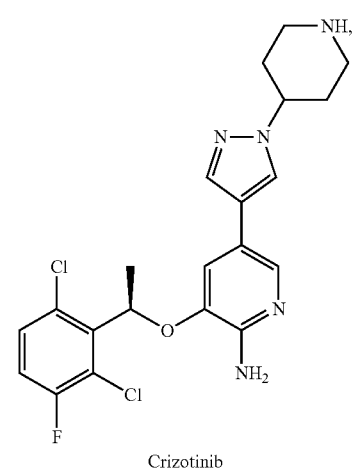
Crizotinib
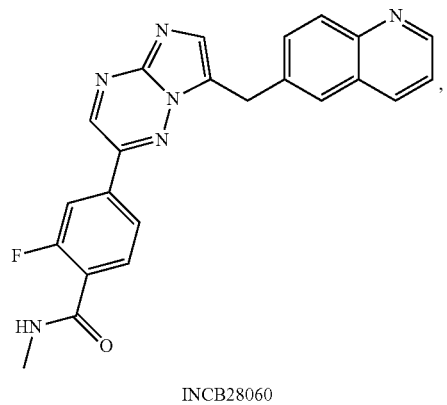
INCB28060
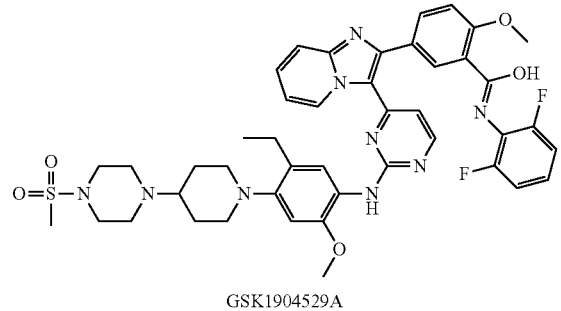
GSK1904529A
-continued
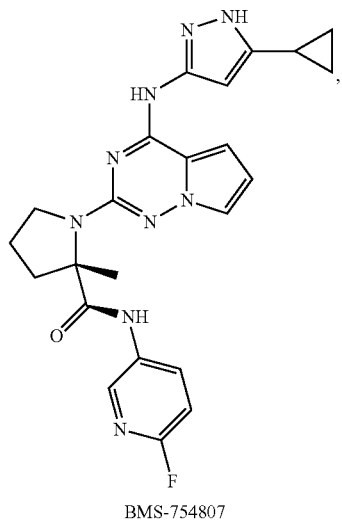
BMS-754807
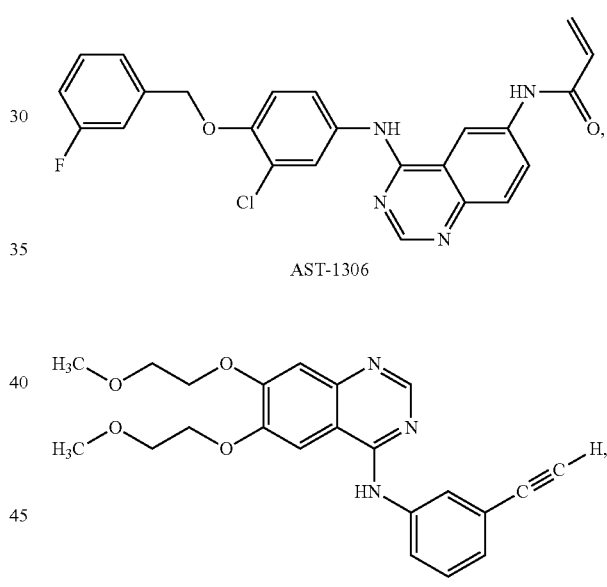
AST-1306
Erlotinib
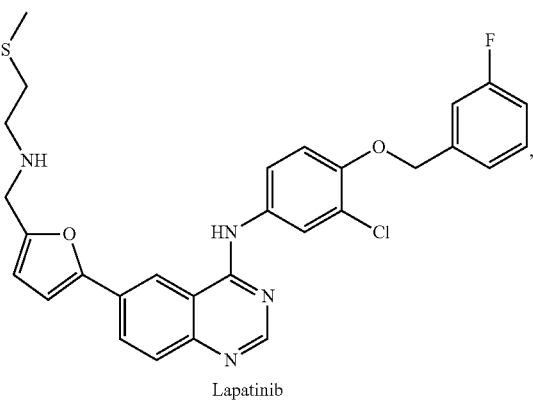
Lapatinib -continued
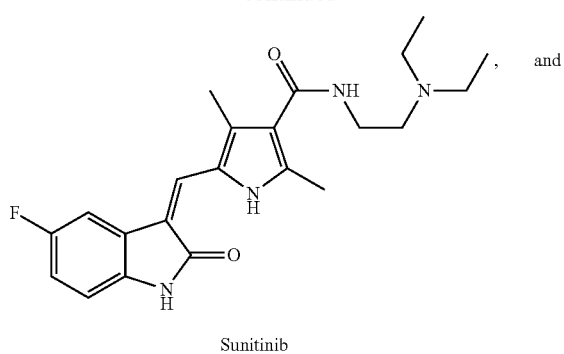
Sunitinib
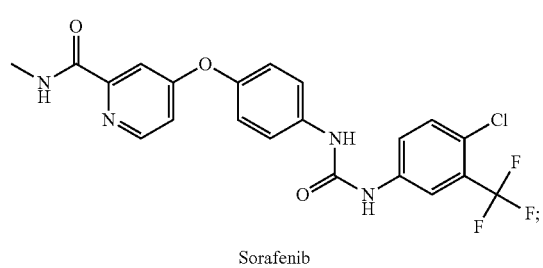
Sorafenib
the phosphoinositide 3-kinase pathway inhibitor is selected from the group consisting of
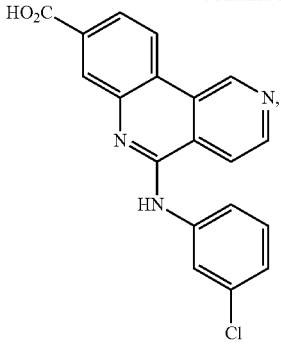
AT7867
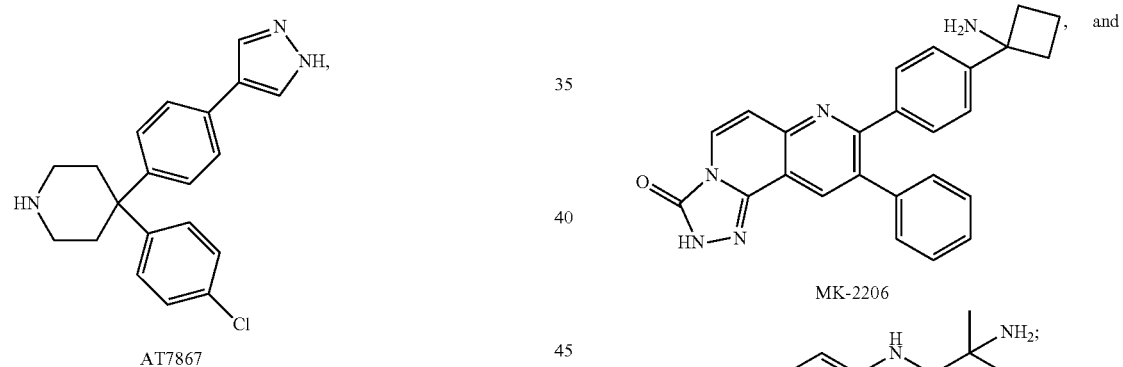
AZD 8055
BX-912
-continued
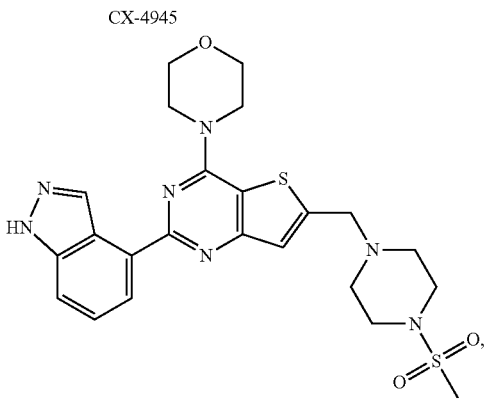
CX-4945
GDC-0941
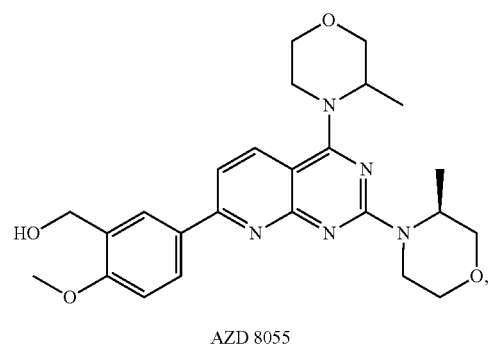
MK-2206
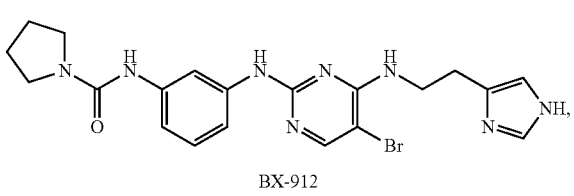
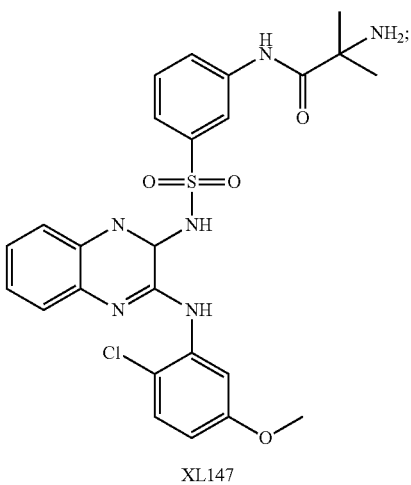
XL147
the serine/threonine-protein kinase and mitogen-activated protein kinase/extracellular signal-regulated protein kinase kinase pathway inhibitor is selected from the group consisting of

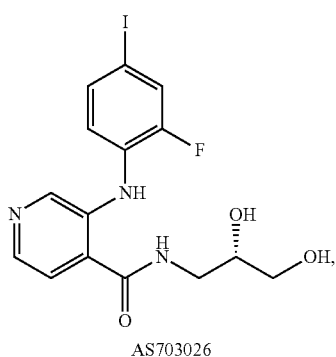
AS703026
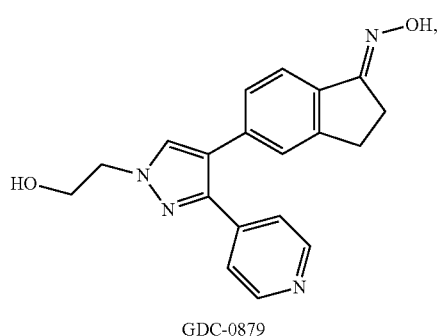
GDC-0879
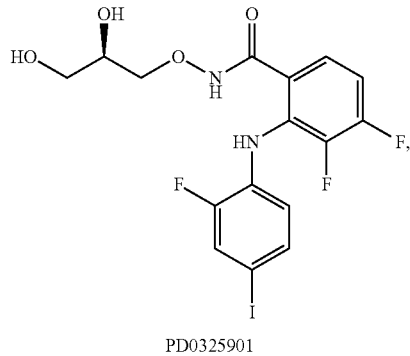
PD0325901
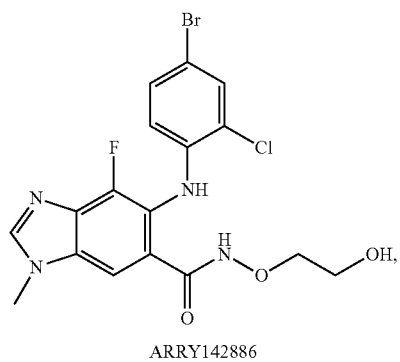
ARRY142886
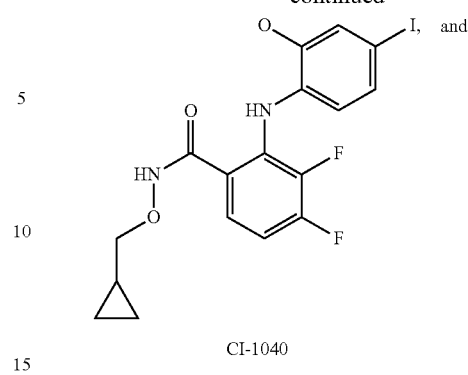
CI-1040
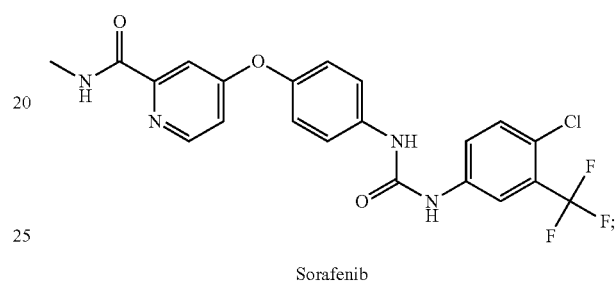
Sorafenib
the deoxyribonucleic acid damaging agent is selected from the group consisting of
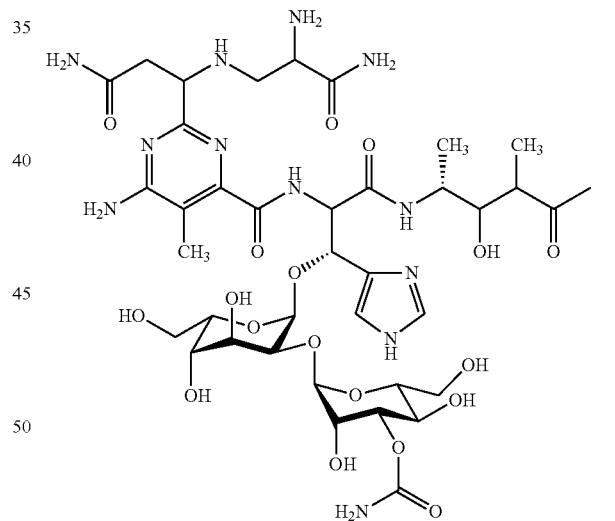
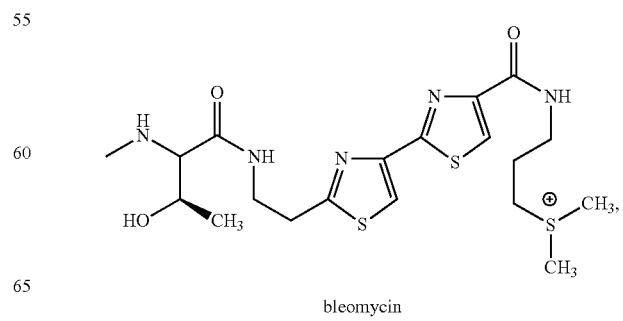
bleomycin

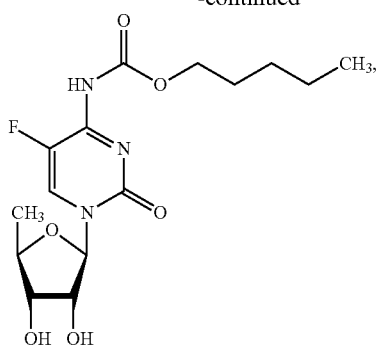
capecitabine
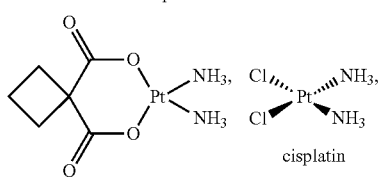
carboplatin    cisplatin
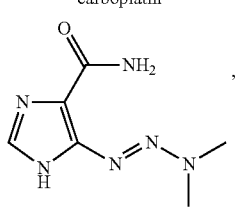
dacarbazine
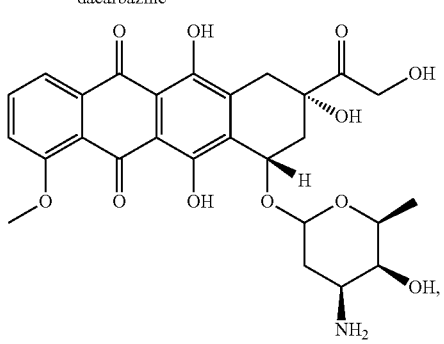
doxorubicin
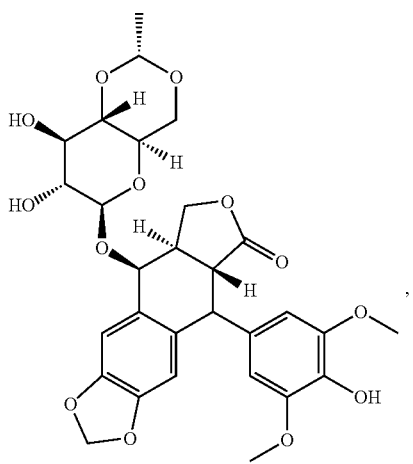
etoposide
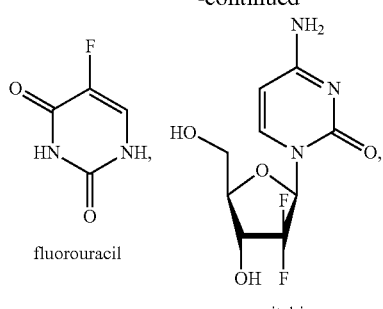
fluorouracil    gemcitabine
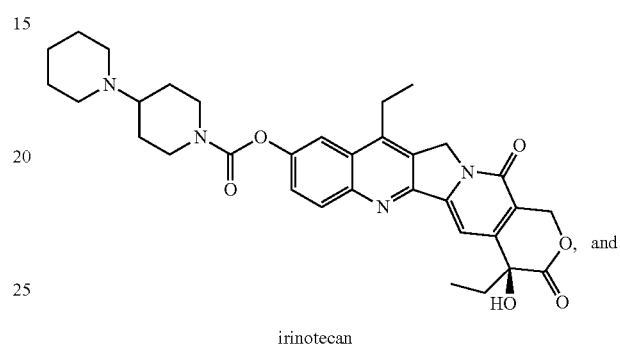
, and
irinotecan
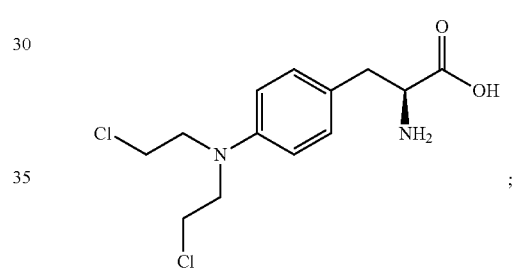
;
melphalan
the deoxyribonucleic acid damage response agent is selected from the group consisting of
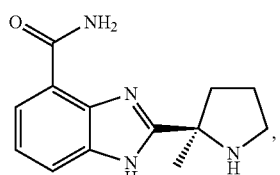
ABT-888
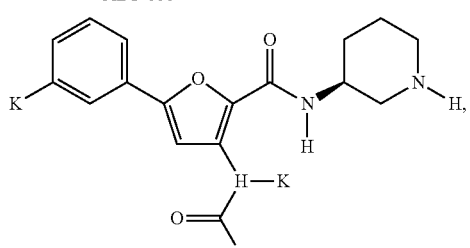
AZD7762

71
-continued
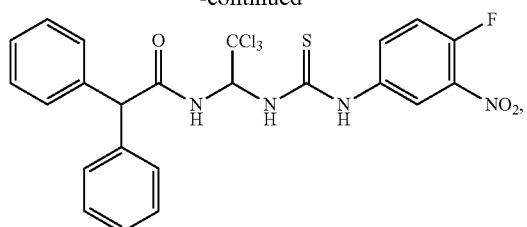
CGK733
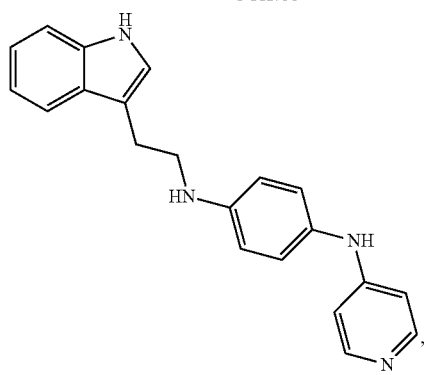
JNJ 26854165
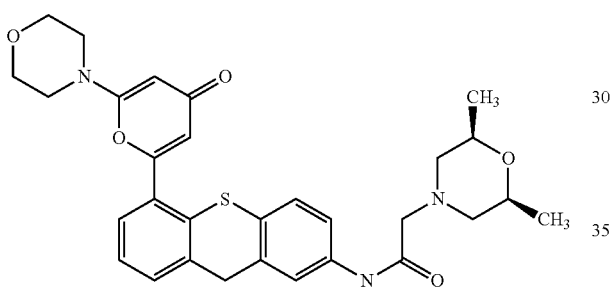
KU-60019
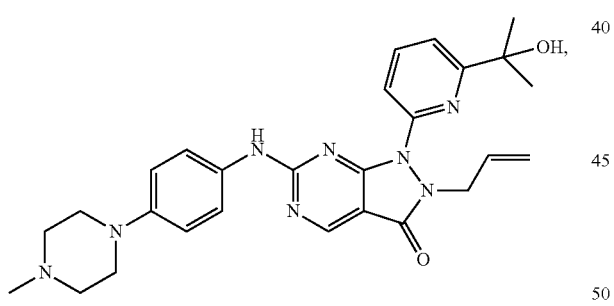
MK-1775
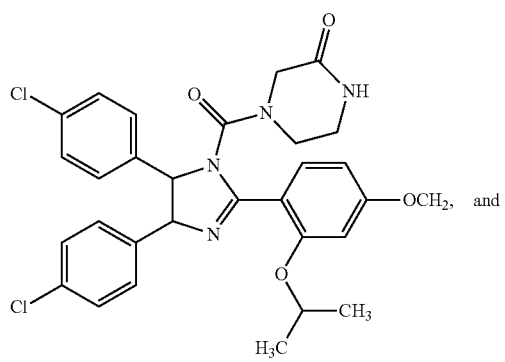
Nutlin-3
72
-continued
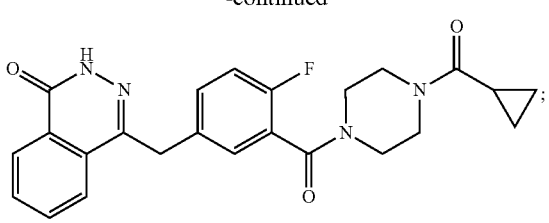
Olaparib
the cytoskeleton perturbagen is selected from the group consisting of
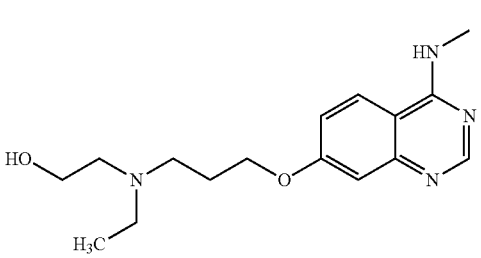
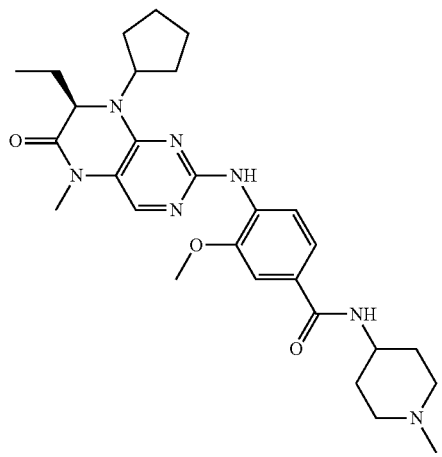
AZD 1152
BI 2536
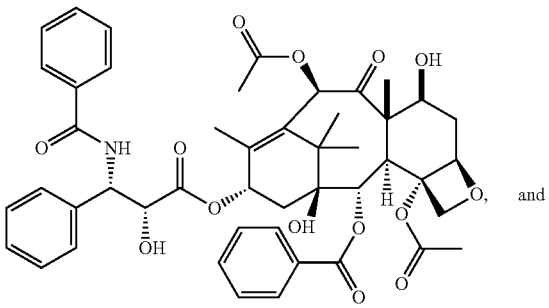
Paclitaxel

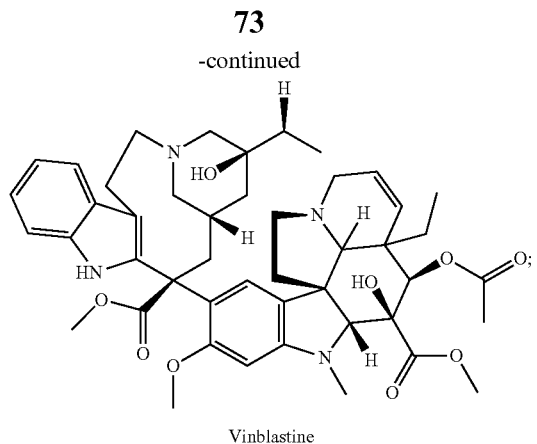
Vinblastine
the protein stability inhibitor is selected from the group consisting of
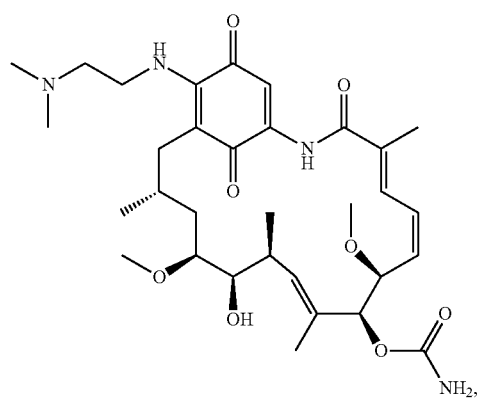
17-DMAG
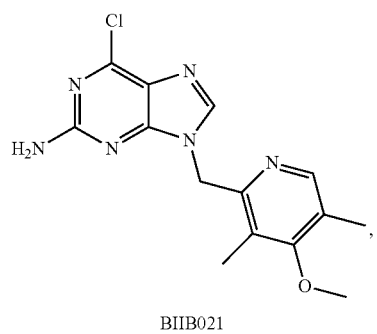
BIIB021
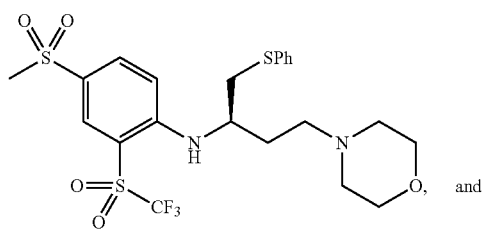
Bortezomib
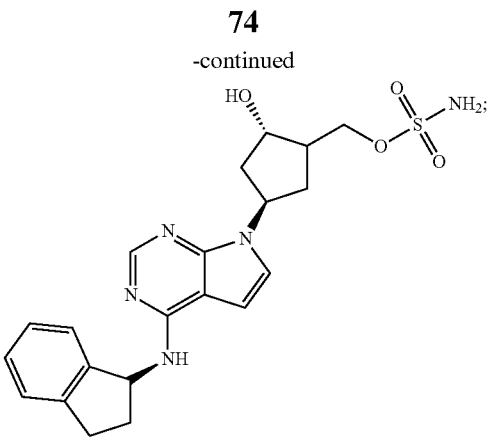
MLN-4924
the Bruton's tyrosine kinase inhibitor is
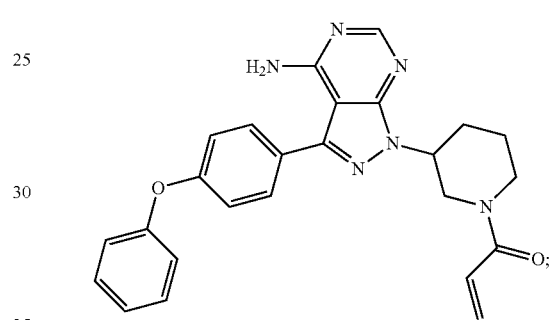
PCI-32765
and
the B-cell lymphoma-2 protein family inhibitor is selected from the group consisting of
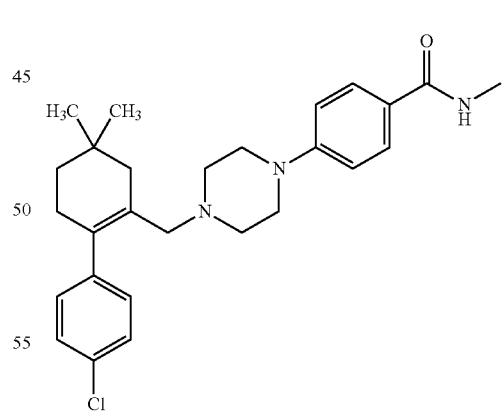
ABT-263
, and

ABT-737

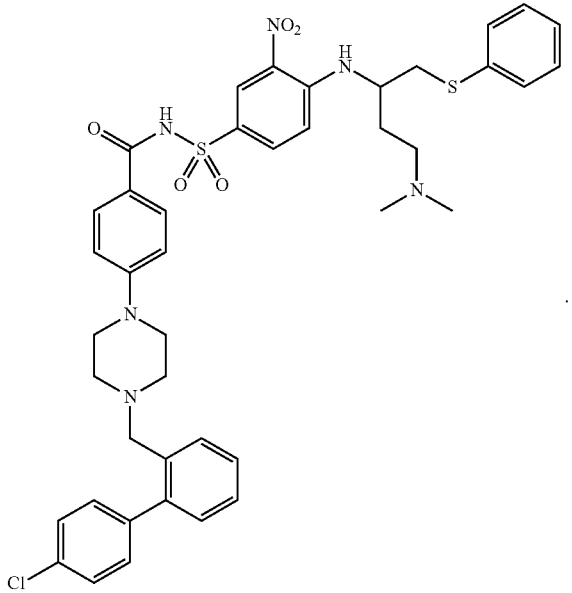

2. The method of claim 1, wherein the patient suffers from a cancer selected from the group consisting of head cancer, neck cancer, eye cancer, mouth cancer, throat cancer, esophagus cancer, bronchus cancer, larynx cancer, pharynx cancer, chest cancer, bone cancer, lung cancer, colon cancer, rectum cancer, stomach cancer, prostate cancer, urinary bladder cancer, uterus cancer, cervix cancer, breast cancer, ovary cancer, testicle cancer, skin cancer, thyroid cancer, blood cancer, kidney cancer, liver cancer, pancreas cancer, brain cancer, a cancer of the lymph nodes, a cancer of the reproductive organs and a cancer of the central nervous system.

3. The method of claim 1, wherein the patient suffers from a cancer associated with the pathways involving a kinase selected from the group consisting of mammalian target of rapamycin kinase, phosphoinositide 3-kinase and protein kinase B.

4. The method of claim 1, wherein the patient suffers from a solid tumor.

5. The method of claim 4, wherein the solid tumor is selected from the group consisting of a neuroendocrine tumor, glioblastoma multiforme, hepatocellular carcinoma, breast cancer, colorectal cancer, salivary cancer, pancreatic cancer, adenocystic cancer, adrenal cancer, esophageal cancer, renal cancer, leiomyosarcoma, paraganglioma, head and neck squamous cell carcinoma, E-twenty six overexpressing castration-resistant prostate cancer and E-twenty six overexpressing Ewing's sarcoma.

6. The method of claim 4, wherein the solid tumor is selected from the group consisting of a relapsed solid tumor and a refractory solid tumor.

7. The method of claim 4, wherein the solid tumor is an advanced solid tumor.

8. The method of claim 1, wherein the second active agent is a receptor tyrosine kinase inhibitor.

9. The method of claim 1, wherein the second active agent is a phosphoinositide 3-kinase pathway inhibitor.

10. The method of claim 1, wherein the second active agent is a serine/threonine-protein kinase and mitogen-activated protein kinase/extracellular signal-regulated protein kinase kinase pathway inhibitor.

11. The method of claim 1, wherein the second active agent is a deoxyribonucleic acid damaging agent.

12. The method of claim 1, wherein the second active agent is a deoxyribonucleic acid damage response agent.

13. The method of claim 1, wherein the second active agent is a cytoskeleton perturbagen.

14. The method of claim 1, wherein the second active agent is a protein stability inhibitor.

15. The method of claim 1, wherein the second active agent is a Bruton's tyrosine kinase inhibitor.

16. The method of claim 1, wherein the second active agent is a B-cell lymphoma-2 protein family inhibitor.

* * * * *